(12) United States Patent
Bradley et al.

(10) Patent No.: US 9,586,992 B2
(45) Date of Patent: Mar. 7, 2017

(54) AMIDATED DOPAMINE NEURON STIMULATING PEPTIDES FOR CNS DOPAMINERGIC UPREGULATION

(71) Applicant: University of Kentucky Research Foundation, Lexington, KY (US)

(72) Inventors: Luke Bradley, Lexington, KY (US); Don Marshall Gash, Lexington, KY (US); Greg Gerhardt, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/153,844

(22) Filed: Jan. 13, 2014

(65) Prior Publication Data

US 2014/0148393 A1    May 29, 2014

Related U.S. Application Data

(60) Division of application No. 12/646,511, filed on Dec. 23, 2009, now abandoned, which is a continuation-in-part of application No. 12/508,916, filed on Jul. 24, 2009, now abandoned, which is a continuation-in-part of application No. 12/447,213, filed as application No. PCT/US2007/022696 on Oct. 26, 2007, now abandoned.

(60) Provisional application No. 60/854,693, filed on Oct. 27, 2006, provisional application No. 61/140,365, filed on Dec. 23, 2008.

(51) Int. Cl.
| | |
|---|---|
| *C07K 7/06* | (2006.01) |
| *A61K 38/08* | (2006.01) |
| *A61K 38/10* | (2006.01) |
| *C07K 7/08* | (2006.01) |

(52) U.S. Cl.
CPC ............... *C07K 7/06* (2013.01); *A61K 38/08* (2013.01); *A61K 38/10* (2013.01); *C07K 7/08* (2013.01)

(58) Field of Classification Search
None
See application file for complete search history.

(56) References Cited

FOREIGN PATENT DOCUMENTS

WO    WO 2005/023861    3/2005

OTHER PUBLICATIONS

Chen et al. "Transgenic Mouse Models of Dopamine Deficiency" Ann Neurol 2003;54 (suppl 6):S91-S102.*
Shah et al. "Current approaches in the treatment of Alzheimer's disease" Biomedicine & Pharmacotherapy 62 (2008) 199-207.*
Sato et al., Synthesis and Circular Dichroism Studies of Oligopeptides Having Tri- or Tetra-L-Prolyl Sequences, Bull. Chem. Soc. Jpn. 1984, 57: 1679-1680.
Fukui et al., Studies of bitter peptides from casein hydrolyzate. I. Synthesis of bitter peptide BPIa corresponding to Arg-Gly-Pro-Pro-Phe-Lle-Val from casein hydrolyzate by alkaline proteinase of Bacilus subtilis, Bull. Chem. Sco. Jpn. 1983, 56: 766-769.
Kundu, Synthesis, Conformational Features and Biological Activity of [Pro3] Antiarrhythmic Peptide, Collect. Czech. Chem. Commun. 1989 54: 760-771.
Kawasaki et al., Amino acids and peptides. XVI. Synthesis of N-terminal tetrapeptide analogs of fibrin .alpha.-chain and their inhibitory effects on fibrinogen/thrombin clotting, Chem. Pharm. Bull. 1992, 40: 3253-3260.
Sofou et al., Synthesis of a proline-rich [60]fullerene peptide with potential biological activity, Tetrahedron 2004, 60: 2823-2828.
Striplin et al., Solvent Dependence of Intramolecular Electron Transfer in a Helical Oligoproline Assembly, J. Am. Chem Soc. 2004, 126: 5282-5291.
T. Immonen etla., A proGDNF-related peptide BEP increases synaptic excitation in rat hippocampus, ScienceDirect, Experimental Neurology 210 2008, pp. 793-796.
Nutt JG, et al. (2003) Randomized, double-blind trial of glial cell line-derived neurotrophic factor (GDNF) in Pd. Neurology. Jan. 14, 2003;60(1):69-73.
Lang AE, et al. (2006) Randomized controlled trial of intraputamenal glial cell line-derived neurotrophic factor infusion in Parkinson disease. Ann Neurol. Mar. 2006;59(3):459-66.
Lo Bianco C, et al. (2004) Lentiviral nigral delivery of GDNF does not prevent neurodegeneration in a genetic rat model of Parkinson's disease. Neurobiology of Disease 17: 283-289.
Marks Jr. et al., (2010) Gene delivery of AAV2-neurturin for Parkinson's disease: a double-blind, randomised, controlled trial. Lancet Neurology. 2010; 9:1164-72.
Decressac M, et al. (2011) GDNF fails to exert neuroprotection in a rat α-synuclein model of Parkinson's disease. Brain 134(8): 2302-2311.
Cullen KM, Halliday GM, Double KL, Brooks WS, Creasey H, Broe GA. Cell loss in the nucleus basalis is related to regional cortical atrophy in Alzheimer's disease. Neuroscience 1997; 78 (3) 641-52.
Lyness SA, Zarow C, Chui HC. Neuron loss in key cholinergic and aminergic nuclei in Alzheimer disease: a meta-analysis. Neurobiol Aging. 2003;24(1):1-23.
Whitehouse PJ, Price DL, Clark AW, Coyle JT, DeLong MR. Alzheimer disease: evidence for selective loss of cholinergic neurons in the nucleus basalis. Ann Neurol. 1981;10(2):122-6.
Whitehouse PJ, Price DL, Struble RG, Clark AW, Coyle JT, Delon MR. Alzheimer's disease and senile dementia: loss of neurons in the basal forebrain. Science. 1982;215(4537):1237-9.

* cited by examiner

*Primary Examiner* — Christina Bradley
(74) *Attorney, Agent, or Firm* — Crowell & Moring LLP

(57) ABSTRACT

The present invention relates to novel proteins, referred to herein as amidated glial cell line-derived neurotrophic factor (GDNF) peptides (or "Amidated Dopamine Neuron Stimulating peptides (ADNS peptides)"), that are useful for treating brain diseases and injuries that result in dopaminergic deficiencies.

8 Claims, 20 Drawing Sheets

Mature Human GDNF

```
TCA CCA GAT AAA CAA ATG GCA GTG CTT CCT AGA AGA GAG CGG AAT
Ser Pro Asp Lys Gln Met Ala Val Leu Pro Arg Arg Glu Arg Asn
         5                   10                      15

CGG CAG GCT GCA GCT GCC AAC CCA GAG AAT TCC AGA GGA AAA GGT
Arg Gln Ala Ala Ala Ala Asn Pro Glu Asn Ser Arg Gly Lys Gly
             20                  25                      30

CGG AGA GGC CAG AGG GGC AAA AAC CGG GGT TGT GTC TTA ACT GCA
Arg Arg Gly Gln Arg Gly Lys Asn Arg Gly Cys Val Leu Thr Ala
                 35                  40                  45

ATA CAT TTA AAT GTC ACT GAC TTG GGT CTG GGC TAT GAA ACC AAG
Ile His Leu Asn Val Thr Asp Leu Gly Leu Gly Tyr Glu Thr Lys
                     50                  55                  60

GAG GAA CTG ATT TTT AGG TAC TGC AGC GGC TCT TGC GAT GCA GCT
Glu Glu Leu Ile Phe Arg Tyr Cys Ser Gly Ser Cys Asp Ala Ala
                         65                  70                  75

GAG ACA ACG TAC GAC AAA ATA TTG AAA AAC TTA TCC AGA AAT AGA
Glu Thr Thr Tyr Asp Lys Ile Leu Lys Asn Leu Ser Arg Asn Arg
                             80                  85                  90

AGG CTG GTG AGT GAC AAA GTA GGG CAG GCA TGT TGC AGA CCC ATC
Arg Leu Val Ser Asp Lys Val Gly Gln Ala Cys Cys Arg Pro Ile
                                 95                  100                 105

GCC TTT GAT GAT GAC CTG TCG TTT TTA GAT GAT AAC CTG GTT TAC
Ala Phe Asp Asp Asp Leu Ser Phe Leu Asp Asp Asn Leu Val Tyr
                                     110                 115                 120

CAT ATT CTA AGA AAG CAT TCC GCT AAA AGG TGT GGA TGT ATC
His Ile Leu Arg Lys His Ser Ala Lys Arg Cys Gly Cys Ile
                                         125                 130
```

FIG. 1

Human Glial-cell Derived Neurotrophic Factor Precursor, isotype 1 (GDNF)

```
  1 MKLWDVVAVCLVLLHTASAFPLPAGKRPPE
 31 APAEDRSLGRRRAPFALSSDSNMPEDYPDQ
 61 FDDVMDFIQATIKRLKRSPDKQMAVLPRRE
 91 RNRQAAAANPENSRGKGRRGQRGKNRGCVL
121 TAIHLNVTDLGLGYETKEELIFRYCSGSCD
151 AAETTYDKILKNLSRNRRLVSDKVGQACCR
181 PIAFDDDLSFLDDNLVYHILRKHSAKRCGC
211 I
```

Signal Peptidase

```
                     FPLPAGKRPPE
 31 APAEDRSLGLRRRAPFALSSDSNMPEDYPDQ
 61 FDDVMDFIQATIKRLKRSPDKQMAVLPRRE
 91 RNRQAAAANPENSRGKGRRGQRGKNRGCVL
121 TAIHLNVTDLGLGYETKEELIFRYCSGSCD
151 AAETTYDKILKNLSRNRRLVSDKVGQACCR
181 PIAFDDDLSFLDDNLVYHILRKHSAKRCGC
211 I
```

"Paired Basics-Specific" endopeptidase
(furin-like protease or PC1) that cleaves on the
carboxy side of KR and RR sequences

```
FPLPAGKR
PPEAPAEDRSLGRR
ERNRQAAAANPENSRGKGRR
```

Carboxypeptidase H that removes C-terminal
K and R residues

```
FPLPAG
PPEAPAEDRSLG
ERNRQAAAANPENSRGKG
```

Peptidylglycine Amidating Monooxygenase (PAM)

```
FPLPA-amide
PPEAPAEDRSL-amide
ERNRQAAAANPENSRGK-amide
```

FIG. 2

Precursor Segments

1. FPLPAGKR

2. KRPPEAPAEDRSLGRR

3. RRERNRQAAAANPENSRGKGRR

FIG. 3

Dopamine Neurons in the Right SN
30 days post G-Peptide Injection

Dopamine Neurons in the Right SN
30 days post G-Peptide Injection

Dopamine Neurons in the Right SN
30 days post G-Peptide Injection

Dopamine Neurons in the Right SN
30 days post G-Peptide Injection hGDNF    PPEAPAEDRSL
rGDNF    LLEAPAEDHSL
mGDNF    LLEAPAEDHSL

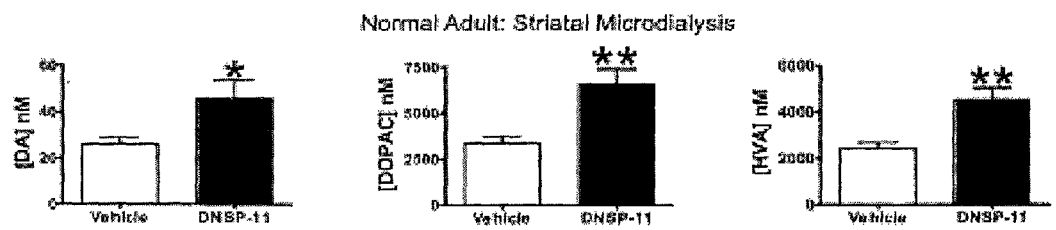
FIG. 12A
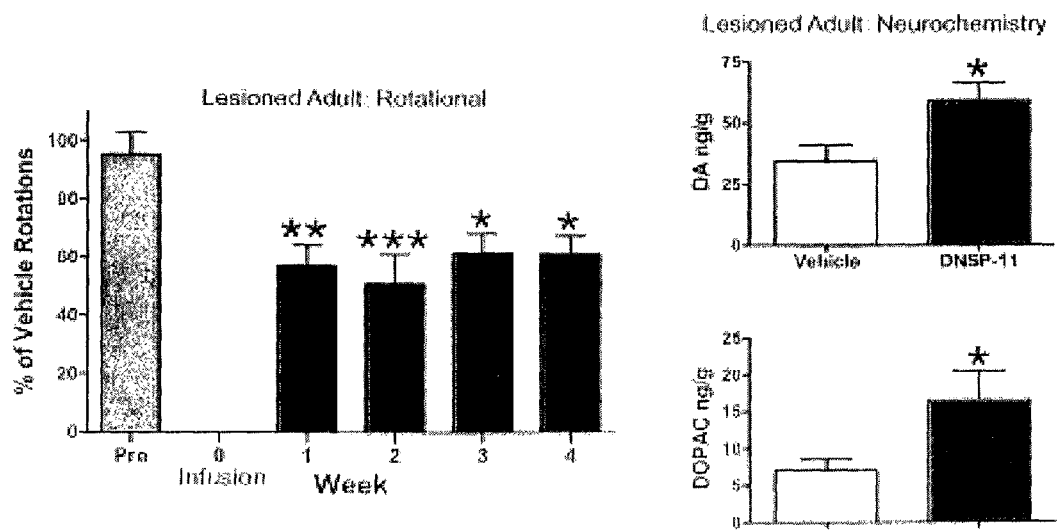
FIG. 12B
FIG. 12C

SEQUENCE LISTING

<160> NUMBER OF SEQ ID NOS: 15

<210> SEQ ID NO 1
<211> LENGTH: 134
<212> TYPE: PRT
<213> ORGANISM: Homo sapiens

<400> SEQUENCE: 1

Ser Pro Asp Lys Gln Met Ala Val Leu Pro Arg Arg Glu Arg Asn Arg
 1               5                  10                  15

Gln Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
    130

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Arg Asn Arg Gln Ala Ala Ala Ala Asn Pro Glu Asn Ser Arg Gly
 1               5                  10                  15

Lys

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Phe Pro Leu Pro Ala
 1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Pro Glu Ala Pro Ala Glu Asp Arg Ser Leu

<210> SEQ ID NO 5
<211> LENGTH: 402
<212> TYPE: DNA
<213> ORGANISM: Homo sapiens
<220> FEATURE:
<221> NAME/KEY: CDS
<222> LOCATION: (1)..(402)

<400> SEQUENCE: 5

```
tca cca gat aaa caa atg gca gtg ctt cct aga aga gag cgg aat cgg    48
Ser Pro Asp Lys Gln Met Ala Val Leu Pro Arg Arg Glu Arg Asn Arg
 1               5                  10                  15 cag gct gca gct gcc aac cca gag aat tcc aga gga aaa ggt cgg aga    96
Gln Ala Ala Ala Ala Asn Pro Glu Asn Ser Arg Gly Lys Gly Arg Arg
             20                  25                  30 ggc cag agg ggc aaa aac cgg ggt tgt gtc tta act gca ata cat tta   144
Gly Gln Arg Gly Lys Asn Arg Gly Cys Val Leu Thr Ala Ile His Leu
         35                  40                  45 aat gtc act gac ttg ggt ctg ggc tat gaa acc aag gag gaa ctg att   192
Asn Val Thr Asp Leu Gly Leu Gly Tyr Glu Thr Lys Glu Glu Leu Ile
     50                  55                  60 ttt agg tac tgc agc ggc tct tgc gat gca gct gag aca acg tac gac   240
Phe Arg Tyr Cys Ser Gly Ser Cys Asp Ala Ala Glu Thr Thr Tyr Asp
 65                  70                  75                  80 aaa ata ttg aaa aac tta tcc aga aat aga agg ctg gtg agt gac aaa   288
Lys Ile Leu Lys Asn Leu Ser Arg Asn Arg Arg Leu Val Ser Asp Lys
                 85                  90                  95 gta ggg cag gca tgt tgc aga ccc atc gcc ttt gat gat gac ctg tcg   336
Val Gly Gln Ala Cys Cys Arg Pro Ile Ala Phe Asp Asp Asp Leu Ser
            100                 105                 110 ttt tta gat gat aac ctg gtt tac cat att cta aga aag cat tcc gct   384
Phe Leu Asp Asp Asn Leu Val Tyr His Ile Leu Arg Lys His Ser Ala
        115                 120                 125 aaa agg tgt gga tgt atc                                           402
Lys Arg Cys Gly Cys Ile
    130
```

<210> SEQ ID NO 6
<211> LENGTH: 211
<212> TYPE: PRT
<213> ORGANISM: Homo sapiens

<400> SEQUENCE: 6

```
Met Lys Leu Trp Asp Val Val Ala Val Cys Leu Val Leu Leu His Thr
 1               5                  10                  15

Ala Ser Ala Phe Pro Leu Pro Ala Gly Lys Arg Pro Pro Glu Ala Pro
             20                  25                  30

Ala Glu Asp Arg Ser Leu Gly Arg Arg Arg Ala Pro Phe Ala Leu Ser
         35                  40                  45

Ser Asp Ser Asn Met Pro Glu Asp Tyr Pro Asp Gln Phe Asp Asp Val
     50                  55                  60

Met Asp Phe Ile Gln Ala Thr Ile Lys Arg Leu Lys Arg Ser Pro Asp
 65                  70                  75                  80

Lys Gln Met Ala Val Leu Pro Arg Arg Glu Arg Asn Arg Gln Ala Ala
                 85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
```

```
                115                 120                 125
Asp Leu Gly Leu Gly Tyr Glu Thr Lys Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
                195                 200                 205

Gly Cys Ile
        210

<210> SEQ ID NO 7
<211> LENGTH: 192
<212> TYPE: PRT
<213> ORGANISM: Homo sapiens

<400> SEQUENCE: 7

Phe Pro Leu Pro Ala Gly Lys Arg Pro Pro Glu Ala Pro Ala Glu Asp
1               5                   10                  15

Arg Ser Leu Gly Arg Arg Arg Ala Pro Phe Ala Leu Ser Ser Asp Ser
                20                  25                  30

Asn Met Pro Glu Asp Tyr Pro Asp Gln Phe Asp Asp Val Met Asp Phe
            35                  40                  45

Ile Gln Ala Thr Ile Lys Arg Leu Lys Arg Ser Pro Asp Lys Gln Met
    50                  55                  60

Ala Val Leu Pro Arg Arg Glu Arg Asn Arg Gln Ala Ala Ala Ala Asn
65                  70                  75                  80

Pro Glu Asn Ser Arg Gly Lys Gly Arg Arg Gly Gln Arg Gly Lys Asn
                85                  90                  95

Arg Gly Cys Val Leu Thr Ala Ile His Leu Asn Val Thr Asp Leu Gly
            100                 105                 110

Leu Gly Tyr Glu Thr Lys Glu Glu Leu Ile Phe Arg Tyr Cys Ser Gly
        115                 120                 125

Ser Cys Asp Ala Ala Glu Thr Thr Tyr Asp Lys Ile Leu Lys Asn Leu
130                 135                 140

Ser Arg Asn Arg Arg Leu Val Ser Asp Lys Val Gly Gln Ala Cys Cys
145                 150                 155                 160

Arg Pro Ile Ala Phe Asp Asp Asp Leu Ser Phe Leu Asp Asp Asn Leu
                165                 170                 175

Val Tyr His Ile Leu Arg Lys His Ser Ala Lys Arg Cys Gly Cys Ile
            180                 185                 190

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Pro Leu Pro Ala Gly Lys Arg
1               5
```

```
<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Pro Glu Ala Pro Ala Glu Asp Arg Ser Leu Gly Arg Arg
 1               5                  10

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Arg Asn Arg Gln Ala Ala Ala Ala Asn Pro Glu Asn Ser Arg Gly
 1               5                  10                  15

Lys Gly Arg Arg
            20

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Pro Leu Pro Ala Gly
 1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Pro Glu Ala Pro Ala Glu Asp Arg Ser Leu Gly
 1               5                  10

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Arg Asn Arg Gln Ala Ala Ala Ala Asn Pro Glu Asn Ser Arg Gly
 1               5                  10                  15

Lys Gly

<210> SEQ ID NO 14
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 14

Lys Arg Pro Pro Glu Ala Pro Ala Glu Asp Arg Ser Leu Gly Arg Arg
 1               5                  10                  15

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Glu Arg Asn Arg Gln Ala Ala Ala Ala Asn Pro Glu Asn Ser
 1               5                  10                  15

Arg Gly Lys Gly Arg Arg
            20
```

AMIDATED DOPAMINE NEURON STIMULATING PEPTIDES FOR CNS DOPAMINERGIC UPREGULATION

CROSS-REFERENCE TO RELATED APPLICATIONS

This application is a divisional of U.S. application Ser. No. 12/646,511, filed Dec. 23, 2009, which is a continuation-in-part of U.S. application Ser. No. 12/508,916, filed Jul. 24, 2009, which is a continuation-in-part of U.S. application Ser. No. 12/447,213 filed Apr. 24, 2009, which is a 371 application of PCT/US2007/022696 filed Oct. 26, 2007, which claims priority of U.S. Application No. 60/854,693 filed Oct. 27, 2006, the disclosures of which are incorporated herein in their entireties. This application claims priority under 35 U.S.C. 119(e) to U.S. Provisional Application No. 61/140,365 filed Dec. 23, 2008, incorporated herein in its entirety by reference.

STATEMENT REGARDING FEDERALLY SPONSORED RESEARCH OR DEVELOPMENT

This invention was made with U.S. government support under grant numbers PO1 AG13494, P50 NS39787-01 and T32 AG000242 awarded by the National Institutes of Health. The U.S. government has certain rights in the invention.

FIELD OF THE INVENTION

The present invention relates to novel proteins, referred to herein as amidated glial cell line-derived neurotrophic factor (GDNF) peptides (or "Amidated Dopamine Neuron Stimulating peptides (ADNS peptides)"), that are useful for treating brain diseases and injuries that result in dopaminergic deficiencies.

BACKGROUND OF THE INVENTION

Neurotrophic factors are endogenous proteins that modulate cell signaling pathways regulating stem cell proliferation, neuronal differentiation, differentiation, growth and regeneration (Barde Y, "*Trophic factors and neuronal survival*", Neuron 2:1525-1534 (1989); Gotz, R., et al., "*The conservation of neurotrophic factors during vertebrate evolution*", Comp Biochem Physiol Pharmacol Toxicol Endocrinol 108: 1-10 (1994); and Goldman, S. A., "*Adult neurogenesis: from canaries to the clinic*", J Neurobiol 36: 267-86 (1998)). They are generally small, soluble proteins with molecular weights between 13 and 24 KDa and often function as homodimers. Because of this physiological role, neurotrophic factors are useful in treating the degeneration of nerve cells and the loss of differentiated function that occurs in a variety of neurodegenerative diseases.

Many neurotrophic factors are both neuroprotective (protecting neurons from injury) and neurorestorative (promoting structural and functional regeneration). The best defined protective functions are seen during neural development. During development, excessive numbers of neurons are generated in many brain regions. Developing neurons that fail to make connections with appropriate trophic factor producing target cells are deprived of necessary neurotrophic factors and die. Those neurons that establish connections survive and function properly (e.g. NGF; see Campenot, R. B. and MacInnis, B. L. "*Retrograde transport of neurotrophins: fact and function*", J Neurobiol 58: 217-229 (2004)). Neurotrophic factors are also capable of promoting the re-growth of damaged neurons and their processes both in vitro and in animal models (see Lad, S. P. et al., "*Individual and combined effects of TrkA and p75NTR nerve growth factor receptors: A role for the high affinity receptor site*", J Biol Chem 278: 24808-24817 (2003a) and Lad, S. P. et al., "*Nerve growth factor: structure, function and therapeutic implications for Alzheimer's disease*", Curr Drug Targets CNS Neurol Disord 2: 315-334 (2003b)). Identifying neurotrophic factors with the right combination of protective and restorative actions and developing effective strategies for drug delivery have profound therapeutic implications for Parkinson's disease, Alzheimer's disease, Huntington's disease and other degenerative processes in the brain (including those induced by brain injury).

Glial cell line-derived neurotrophic factor (GDNF) is a trophic factor shown to dramatically protect and enhance the function of dopamine neurons in vitro and in vivo in rodents and monkeys (Beck, K. D., et al., "*Mesencephalic dopaminergic neurons protected by GDNF from axotomy-induced degeneration in the adult brain*", Nature, 373:339-41 (1995); and Bjorklund, A., et al., "*Towards a neuroprotective gene therapy for Parkinson's disease: use of adenovirus, AAV and lentivirus vectors for gene transfer of GDNF to the nigrostriatal system in the rat Parkinson model*", Brain Res., 886:82-98 (2000), Gash, D. M., et al., "*Functional Recovery in Parkinsonian Monkeys Treated with GDNF*, Nature*", 380:252-255 (1996); Grondin, R., et al., "*Striatal GDNF Infusion Promotes Structural and Functional Recovery in Advanced Parkinsonian Monkeys. Brain*", 125:2191-2201 (2002); Grondin, R., et al., "*GDNF Increases Stimulus-evoked Dopamine Release and Motor Speed in Aged Rhesus Monkeys*", J. Neurosci., 23:1974-1980 (2003); Hebert M. A., et al., "*Functional Effects of GDNF in Normal Rat Striatum: Presynaptic Studies Using In Vivo Electrochemistry and Microdialysis*", J. Pharm. Exp. Ther., 279:1181-1190 (1996); Hebert M. A. and Gerhardt, G. A., "*Behavioral and Neurochemical Effects of Intranigral GDNF Administration on Aged Fischer 344 Rats*", J. Pharm. Exp. Ther., 282: 760-768 (1997); Hou, J. G. G., et al., "*Glial Cell line-Derived Neurotrophic Factor Exerts Neurotrophic Effects on Dopaminergic Neurons In Vitro and Promotes Their Survival And Regrowth After Damage by 1-Methyl-4-Phenylpyridinium*", J. Neurochem., 66: 74-82 (1996); Kordower, J. H., et al., "*Clinicopathological Findings Following Intraventricular Glial-Derived Neurotrophic Factor Treatment in a Patient with Parkinson's Disease*", Ann Neurol., 46(3):419-424 (1999); Kordower, J. H., et al., "*Neurodegeneration Prevented by Lentiviral Vector Delivery of GDNF in Primate Models of Parkinson's Disease*", Science, 290: 767-773 (2000); Palfi, S., et al., "*Lentivirally Delivered Glial Cell Line-derived Neurotrophic Factor Increases the Number of Striatal Dopaminergic Neurons in Primate Models of Nigrostriatal Degeneration*", J. Neurosci., 22:4942-4954 (2002); Tomac, A., et al., "*Protection and Repair of the Nigrostriatal Dopaminergic System by GDNF In Vivo*", Nature, 373:335-339 (1995)).

The current standard treatment, levodopa, is palliative and does not prevent the relentless progression of Parkinson's degeneration. GDNF exerts effects on dopamine neurons that slow the process of Parkinson's disease and even reverses some of the degenerative changes. Preclinical studies conducted to date suggest that GDNF exerts at least three general trophic actions on dopamine neurons in the substantia nigra: pharmacological upregulation, restoration and neuroprotection. With regard to pharmacological upregulation, GDNF upregulates dopaminergic functions, such as increasing the evoked release of dopamine (Gerhardt, G. A. et al., "*GDNF improves dopamine function in the substantia nigra but not the putamen of unilateral MPTP-lesioned rhesus monkeys*", Brain Res 817: 163-171 (1999) and Grondin et al., 2003). It also appears to modulate the phosphorylation of TH (Salvatore, M. et al. "Striatal GDNF administration increases tyrosine hydroxylase phosphorylation in the rat striatum and substantia nigra". *J Neurochem.* 90:245-54, (2004)). With regard to restoration, GDNF increases the number of neurons expressing the dopamine markers TH and DAT in the substantia nigra (Gash et al., 1996; Kordower et al., 2000; and Grondin et al., 2002). This suggests that one trophic action is to stimulate recovery of injured/quiescent nigral neurons. Supporting this interpretation is the consistent observation that GDNF promotes increases in dopamine neuron perikaryal size and the number of neurites. With regard to neuroprotection, nigrostriatal administration of GDNF either shortly before or following a neurotoxic challenge (e.g. 6-OHDA, methyl-amphetamine or MPTP) protects dopamine neurons from injury in rodents and non-human primates (Kordower et al., 2000 and Fox, C. M., "*Neuroprotective effects of GDNF against 6-OHDA in young and aged rats*", Brain Res 896:56-63 (2001)).

Accordingly, GDNF therapy is expected to be helpful in the treatment of nerve damage caused by conditions that compromise the survival and/or proper function of one or more types of nerve cells. Such nerve damage may occur from a wide variety of different causes. Nerve damage may occur to one or more types of nerve cells by, for example: (1) physical injury, which causes the degeneration of the axonal processes and/or nerve cell bodies near the site of injury; (2) temporary or permanent cessation of blood flow to parts of the nervous system, as in stroke; (3) intentional or accidental exposure to neurotoxins, such as chemotherapeutic agents (e.g., cisplatinum) for the treatment of cancer or dideoxycytidine (ddC) for the treatment of AIDS; (4) chronic metabolic diseases, such as diabetes or renal dysfunction; or (5) neurodegenerative diseases such as Parkinson's disease, Alzheimer's disease, and Amyotrophic Lateral Sclerosis (ALS), which result from the degeneration of specific neuronal populations.

GDNF therapy may be particularly helpful in the treatment of neurodegenerative conditions involving the degeneration of the dopaminergic neurons of the substantia nigra, such as Parkinson's disease. The expected impact of GDNF therapy is not just to produce an increase in the dopaminergic neurotransmission at the dopaminergic nerve terminals in the striatum (which will result in a relief of the symptoms), but also to slow down, or even stop, the progression of the degenerative processes and to repair the damaged nigrostriatal pathway and restore its function. GDNF may also be used in treating other forms of damage to or improper function of dopaminergic nerve cells in human subjects. Such damage or malfunction may occur in schizophrenia and other forms of psychosis. The only current treatments for such conditions are symptomatic and require drugs which act upon dopamine receptors or dopamine uptake sites, consistent with the view that the improper functioning of the dopaminergic neurons which innervate these receptor-bearing neuronal populations may be involved in the disease process.

However, initial clinical trials involving ventricular delivery of GDNF showed no statistically significant differentiation of the placebo and active treatment groups (Nutt, J. G. et al. "*Randomized, double-blind trial of glial cell line-derived neurotrophic factor (GDNF) in PD*", Neurology 60: 69-73 (2003)), perhaps because insufficient amounts of GDNF reached critical target sites from the CSF (Ai, Y. et al., "*Intraputamenal Infusion in Aging Rhesus Monkeys: Distribution and Dopaminergic Effects*", J Comp Neurol 461: 250-26125 (2003); and Kordower, J. H., et al. (2000)). In addition, a phase 2 trial evaluating intraputamenal delivery of glial cell line-derived neurotrophic factor (GDNF) for the treatment of Parkinson's disease failed to achieve its primary end point, a 25% improvement on the Unified Parkinson Disease Rating Scale (UPDRS) motor score "off" medication after six months of treatment (Lang, A. E. et al., "*Randomized controlled trial of intraputamenal glial cell line-derived neurotrophic factor infusion in Parkinson's disease*", Ann Neurol 59:459-466 (2006)). There are strong indications from studies in rhesus monkeys using the same delivery system and protocol followed in the phase 2 study that drug bioavailability significantly contributed to the failure of the trial (Salvatore et al., "*Point source concentration of GDNF may explain failure of phase II clinical trial*". Exp Neurol 202 (2): 497-505 (2006)). The concentration of GDNF around the catheter tip and limited diffusion into surrounding brain parenchyma was limited to a brain volume representing 2-9% of the human putamen. Thus GDNF distribution in the phase 2 trial was likely limited to a small brain region, and could affect only a limited segment of the brain undergoing parkinsonian degeneration.

Successful trophic factor therapy requires site-specific delivery and distribution of the trophic factor throughout the target tissue (the putamen for Parkinson's disease). The blood brain barrier effectively blocks entry from blood borne proteins, including trophic factors. Infusions into the cerebrospinal fluid are not effective in humans because of brain size and may produce unwanted side effects by stimulating other trophic factor responsive populations such as sensory neurons.

In addition to focal delivery into the appropriate site, the delivery must be tightly regulated. Regardless of the method used to deliver GDNF (i.e., direct infusion, stem cells, encapsulated cells, gene therapy) prolonged elevated levels of GDNF in the brain outside of the target area may produce adverse side-effects. Circulating antibodies to GDNF are one possible outcome and it is quite typical to find antibodies to endogenous proteins used therapeutically (e.g. beta interferon and insulin, see Durelli, L., et al., "*Anti-interferon antibodies in multiple sclerosis: molecular basis and their impact on clinical efficacy*", Front Biosci 9: 2192-2204 (2004) and Stoever, J. A. et al., "*Inhaled insulin and insulin antibodies: a new twist to an old debate*", Diabetes Technol Ther 4: 157-161 (2002)). The effects of circulating GDNF antibodies are not known. Focal Purkinje cell lesions have been reported in some monkeys receiving high levels of GDNF in a toxicology study (see Sherer, T. B., et al., Movement Dis 21:136-141 (2006)). Another possible side-effect is aberrant sprouting and tyrosine hydroxylase down-regulation of the nigrostriatal dopaminergic pathway in rats exposed to high GDNF levels from viral vector gene transfer (Georgievska, B., et al. "*Neuroprotection in the rat Parkinson model by intrastriatal GDNF gene transfer using a lentiviral vector*", Neuroreport 13: 75-82 (2002)). Also, increased neuronal death has been reported in rats with elevated GDNF from viral vector gene transfer in a stroke model (Arvidsson, A. et al., "*Elevated GDNF levels following viral vector-mediated gene transfer can increase neuronal death after stroke in rats*", Neurobiol Dis 14: 542-556, (2003)).

While GDNF has not met the criteria for clinical efficacy in the two phase 2 trials conducted to date (Nutt et al., 2003; Lang et al., 2006), it appears to be the most potent dopaminergic trophic factor found to date. Thus, the ideal drug for treating Parkinson's disease and other neurodegenerative processes in the brain would possess the positive trophic actions of GDNF. Delivery could be targeted to the appropriate brain area by any of a number of methods including direct infusion, viral vectors or even nasal sprays. In particular, biologically active peptides with trophic actions may offer many of the desired properties. To date, such biologically active peptides have not been identified.

A crude peptide extract from the brain cerebrolysin has been tested in human studies, with modest effects reported (Lukhanina, E. P. et al., "*Effect of cerebrolysin on the electroencephalographic indices of brain activity in Parkinson's disease*", Zh Nevrol Psikhiatr Im S S Korsakova 104: 54-60 (2004)). Three small molecule compounds have also been tested in Parkinson's disease patients: the tripeptide glutathione, tocopherol, and Coenzyme Q10 (Weber, C. A., et al. "*Antioxidants, supplements and Parkinson's disease*", Ann Pharmacother 40: 935-938 (2006)). The three small molecule compounds also appear to have only minor benefits for patients.

Consequently, there continues to exist a long-felt need for effective agents and methods for the treatment and prevention of brain diseases and injuries that result in dopaminergic deficiencies. Accordingly, it is an object of the present invention to provide agents for treating and preventing such diseases and injuries in a subject, comprising novel amidated GDNF-derived peptides that have dopaminergic trophic factor activity. This and other such objectives will be readily apparent to the skilled artisan from this disclosure.

SUMMARY OF THE INVENTION

In one embodiment, the present invention provides a composition comprising at least one of the following peptides: (a) a purified Amidated Dopamine Neuron Stimulating peptide (ADNS peptide) comprising the amino acid sequence ERNRQAAAANPENSRGK-amide (SEQ ID NO: 2); (b) a purified ADNS peptide comprising the amino acid sequence FPLPA-amide (SEQ ID NO: 3); and (c) a purified ADNS peptide comprising the amino acid sequence PPEAPAEDRSL-amide (SEQ ID NO: 4). In another embodiment, the present invention provides a method for treating a brain disease or injury resulting in dopaminergic deficiencies, comprising administering a pharmaceutically effective amount of the composition to a subject in need thereof, wherein said composition further comprises at least one of a pharmaceutically acceptable vehicle, excipient, and diluent. Preferably, the subject is a mammal, and most preferably, the subject is human.

BRIEF DESCRIPTION OF THE FIGURES

FIG. 1 depicts the nucleotide sequence (top strand) and amino acid sequence (bottom strand) of mature human GDNF (SEQ ID NO: 5 and SEQ ID NO: 1).

FIG. 2 depicts the post-translational processing of splice form 1 of human GDNF. Sequences from top to bottom are: SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 3, SEQ ID NO:4, and SEQ ID NO: 2.

FIG. 3 depicts the precursor segments of the ADNS peptides ERNRQAAAANPENSRGK-amide (SEQ ID NO: 2), FPLPA-amide (SEQ ID NO:3), and PPEAPAEDRSL-amide (SEQ ID NO:4). From top to bottom SEQ ID NO: 8, SEQ ID NO: 14, and SEQ ID NO:15.

FIGS. 12A-C depict the effects of DNSP-11 in normal (A) and unilateral 6-OHDA-lesioned (B and C) rats.

DETAILED DESCRIPTION OF THE INVENTION

Figure 4:
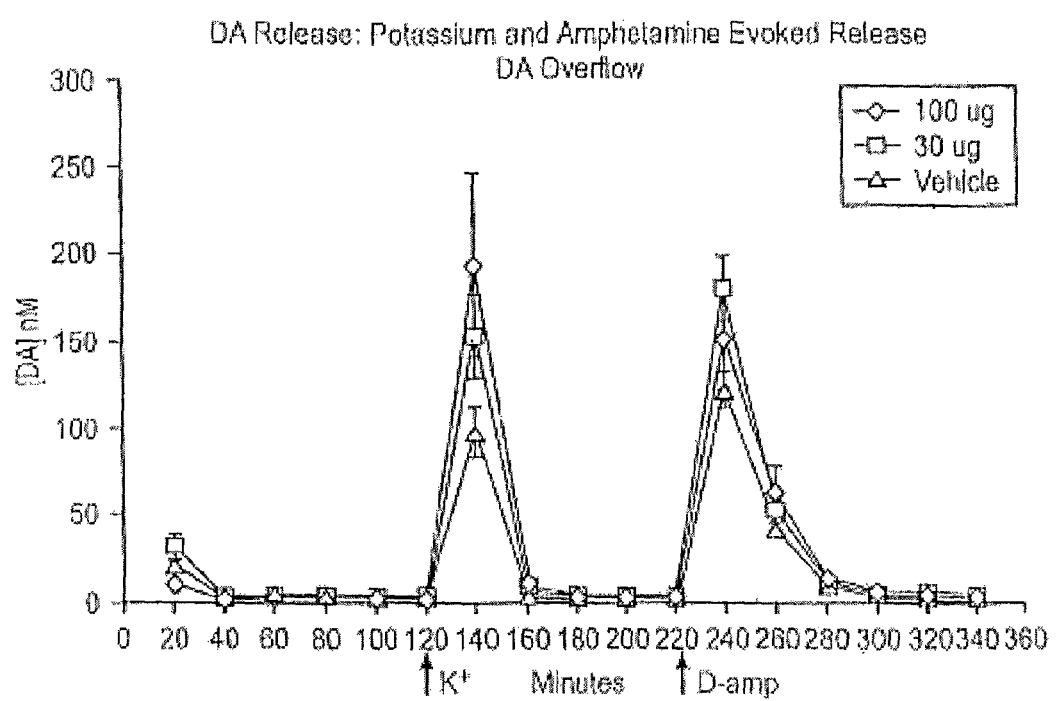
FIG. 4 depicts the average $K^+$-evoked release of dopamine in Fischer 344 rats treated with ADNS peptides.

Human glial cell line-derived neurotrophic factor (hGDNF) is synthesized as a precursor that is processed and secreted as a mature protein of 134 amino acids. Mature human GDNF has the amino acid sequence depicted in FIG. 1 (SEQ ID NO:1).

The present invention is related to the realization that human GDNF (splice form 1) precursor protein conforms to a rather exacting sequence profile characteristic of neuropeptide precursor proteins. GDNF is expressed in at least three isoforms that result from alternative splicing of mRNA. Proteins expressed from these RNA splice variants differ in their N-terminal regions (see NCBI entry NP 000505 for isoform 1; NCBI entry NP 964701 for isoform 2; and NCBI entry NP 954704 for isoform 3). Isoforms 1 and 2 are secretory protein precursors with N-terminal signal peptides. Isoform 3 is likely a nuclear-targeted protein with a nuclear localization signal (NLS), but no signal peptide. The three isoforms are differentially expressed, apparently under regulatory control.

All of the isoforms contain the sequence that is considered mature GDNF with "full biological activity" (residues 78-211 in isoform 1). In fact, recombinant proteins further truncated at the N-terminus are purported to have the "full biological activity". From the fact that three separate precursors of the same GDNF molecule are expressed under separate regulation, two with signal peptides and the third with a probable nuclear localization signal, suggests that there are both nuclear and cell surface receptors for GDNF.

The separately regulated expression of two different secretory isoforms (isoforms 1 and 2) suggests a biologically significant function for the different N-terminal sequences of the isoforms. The conventional wisdom is that residues 20-77 of isoform 1 precursor constitute a "domain propeptide". The present invention provides a new interpretation of the importance of the 20-77 "domain propeptide" region of isoform 1 precursor. The "domain propeptide" segment of isoform 1 precursor is the metabolic precursor of two small amidated peptides, according to well established enzymatic pathways for release of peptide amide hormones and neuropeptides from their precursor proteins. The two small amidated peptides are FPLPA-amide (SEQ ID NO: 3) and PPEAPAEDRSL-amide (SEQ ID NO: 4).

Furthermore, a third small amidated peptide, ERNRQAAAANPENSRGK-amide (SEQ ID NO: 2), may be released from consensus enzymatic processing of residues 88-110 of the isoform 1 precursor. This consensus peptide amide precursor occupies the N-terminal sequence of "mature GDNF", which is presumably not critical or at least includes residues that are not critical for biological activity, according to the patent literature. The isoform 2 precursor contains the sequence FPLPA (SEQ ID NO: 16), but does not contain the amidation signal (GKR, residues 25-27) in the case of Isoform 1 precursor. Isoform 2 is not, in other words, a potential precursor of FPLPA-amide (SEQ ID NO: 3) according to known enzymatic pathways. Isoform 3 does not contain the sequence FPLPA at all, so likewise can not be a metabolic precursor of FPLPA-amide (SEQ ID NO: 3). Both Isoforms 1 and 2 are consensus precursors of ERNRQAAAANPENSRGK-amide (SEQ ID NO: 2), but isoform 3 is not.

Thus, human GDNF isoform 1 is a secretory protein that can potentially yield three small amidated peptides by consensus enzymatic pathways known to release peptide amide hormones and neuropeptides from their known precursor proteins. This is a rare combination of enzymatic processing motifs and strongly suggests that GDNF isoform 1 precursor is the metabolic precursor of up to three small ADNS peptides, in addition to the larger C-terminal domain that is widely supposed to posses the "full biological activity" of GDNF. C-terminal amidation in natural peptides is highly correlated with receptor mediated signal transduction: about half of the known peptide hormones and neuropeptides and C-terminal amidation is rare and almost unknown among other peptides of biological origin.

Animal studies with synthetic peptides corresponding to the consensus products of Isoform 1 precursor protein are consistent with some or all of these peptides being biologically active and involved in regulation of dopamine metabolism. This is to be expected from a protein that yields multiple biologically active regulatory peptides in a fixed molar ratio. The fact that the different Isoforms of GDNF precursor protein are consensus precursors of different combinations of amidated peptides in addition to GDNF, suggests a reason for differential expression of three separate isoforms (in addition to differential secretory and nuclear routing).

According to this model, splice form 1 of human GDNF may be post-translationally processed in vivo to yield three small amidated peptides, as indicated in FIG. 2. These small amidated peptides may mediate some or all of the biological effects of GDNF. The present invention is based on the unexpected discovery that these small amidated fragments of the mature GDNF protein retain the biological activity of GDNF.

Thus, the ADNS peptides of the present invention include these three small amidated peptides, which are represented by the amino acid sequences ERNRQAAAANPENSRGK-amide; FPLPA-amide; and PPEAPAEDRSL-amide (SEQ ID NOs:2, 3, and 4, respectively).

The ADNS peptides of the present invention are promising candidates for treatment and prevention of neurodegenerative conditions involving dopaminergic deficiencies, such as Parkinsons disease, age-associated motor and cognitive slowing, and other diseases and injuries to the brain. The small ADNS peptides are easily within the range of synthetic production methods, so that the molecules could be subjected to rigorous structure-activity studies to optimize pharmacological activities and biostability. In addition, as the difficulties in delivering GDNF clinically may well be related to the fact that recombinant GDNF is not properly processed into active forms, the small ADNS peptides may overcome some of these difficulties. Finally, small peptides are generally much less antigenic than proteins and can be synthesized free of the trace host protein contaminants always present in recombinant proteins.

The small ADNS peptides of the present invention include biologically active synthetic or recombinant ADNS peptides, ADNS peptides produced from GDNF, biologically active ADNS peptide variants (including insertion, substitution, and deletion variants), and chemically modified derivatives thereof. Also included are biologically active ADNS peptide variants that are substantially homologous to any one of the ADNS peptides having the amino acid sequence set forth in SEQ ID NOs:2, 3, or 4.

The term "biologically active" as used herein means that the ADNS peptide demonstrates similar neurotrophic properties, but not necessarily all of the same properties, and not necessarily to the same degree, as the GDNF protein having the amino acid sequence set forth in SEQ ID NO:1. The selection of the particular neurotrophic properties of interest depends upon the use for which the ADNS peptide is being administered. The ADNS peptides are biologically active and demonstrate dopaminergic neuron survival characteristics similar to that demonstrated by the combination of amide peptides represented by SEQ ID NOs:2, 3, or 4 using the evaluation of dopamine neuron survival in cultures of newborn rat midbrain dopamine neurons as an exemplary bioassay, as discussed in the examples below.

The term "substantially homologous", as used herein, means a degree of sequence homology to any one of the ADNS peptides having the amino acid sequences set forth in SEQ ID NOs:2, 3, or 4 that is preferably at least 70%, most preferably at least 80%, and even more preferably at least 90% or even 95%.

As used herein, the term "ADNS peptide," "peptide amide," or "amidated peptide" means a peptide comprising the group —$CONH_2$ at the C-terminal end. This amidation occurs in vivo, once the peptides are formed by the enzyme, peptidylglycine amidating monooxygenase (PAM). The ADNS peptides of the present invention can be readily obtained in a variety of ways, including, without limitation, recombinant expression, purification from natural sources, and/or chemical synthesis. Preferably, the ADNS peptides can be chemically synthesized by commercial venders. The ADNS peptides used in the present examples were synthesized using tBOC chemistry and at a single scale range (which generates a theoretical crude yield of 500-1,000 mg for a 10-20 mer respectively), by the Keck Biotechnology Resource Laboratory at Yale University (New Haven, Conn.).

ADNS peptide pharmaceutical compositions typically include a therapeutically effective amount of at least one of a ADNS peptide represented by SEQ ID NOs:2, 3, and 4 in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial cerebrospinal fluid (CSF), possibly supplemented with other materials common in compositions for parenteral administration. Neutral buffered saline or saline mixed with serum albumin are further exemplary vehicles.

The primary solvent in a vehicle may be either aqueous or non-aqueous in nature. In addition, the vehicle may contain other pharmaceutically-acceptable excipients for modifying or maintaining the pH, osmolarity, viscosity, clarity, color, sterility, stability, rate of dissolution, or odor of the formulation. Similarly, the vehicle may contain still other pharmaceutically-acceptable excipients for modifying or maintaining the stability, rate of dissolution, or rate of release of ADNS peptide, or for promoting the absorption or penetration of ADNS peptide across the blood-brain barrier. Such excipients are those substances usually and customarily employed to formulate dosages for parenteral administration in either unit dose or multi-dose form or for direct infusion into the CSF by continuous or periodic infusion from an implanted pump.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration.

The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712 the disclosure of which is hereby incorporated by reference. The composition may also involve particulate preparations of polymeric compounds such as polylactic acid, polyglycolic acid, etc. or into liposomes. Hylauronic acid may also be used, and this may have the effect of promoting sustained duration in the circulation. Such compositions may influence the physical state, stability, rate of in vivo release, and rate of in vivo clearance of the present proteins and derivatives.

Other effective administration forms, such as parenteral slow-release formulations, inhalant mists, orally active formulations, or suppositories, are also envisioned. Preferred ADNS peptide pharmaceutical compositions are formulated for parenteral administration, e.g., intracerebroventricular injection. Such parenterally administered therapeutic compositions are typically in the form of a pyrogen-free, parenterally acceptable aqueous solution comprising ADNS peptide in a pharmaceutically acceptable vehicle. One preferred vehicle is physiological saline.

It is also contemplated that certain formulations containing ADNS peptides are to be administered orally. ADNS peptide which is administered in this fashion may be encapsulated and may be formulated with or without those carriers customarily used in the compounding of solid dosage forms. The capsule may designed to release the active portion of the formulation at the point in the gastrointestinal tract when bioavailability is maximized and pre-systemic degradation is minimized. Additional excipients may be included to facilitate absorption of ADNS peptide.

Diluents, flavorings, low melting point waxes, vegetable oils, lubricants, suspending agents, tablet disintegrating agents, and binders may also be employed.

It is further contemplated that formulations containing ADNS peptides are to be administered nasally. As used herein, nasally administering or nasal administration includes administering the formulation containing ADNS to the mucous membranes of the nasal passage or nasal cavity of the patient. Formulations for nasal administration include a pharmaceutically effective amount of the peptides prepared by well-known methods, to be administered, for example, as a nasal spray, drop, suspension, gel, ointment, cream or powder. Administration of the ADNS-containing formulation may also take place using a nasal tampon, or nasal sponge.

The ADNS peptides may be administered parenterally via a subcutaneous, intramuscular, intravenous, transpulmonary, transdermal, intrathecal or intracerebral route. ADNS peptides that do not cross the blood-brain barrier may be given directly intracerebrally or otherwise in association with other elements that will transport them across the barrier. It is preferred that the ADNS peptide is administered intracerebroventricularly or into the brain or spinal cord subarachnoid space. ADNS peptides may also be administered intracerebrally directly into the brain parenchyma. Slow-releasing implants in the brain containing the neurotrophic factor embedded in a biodegradable polymer matrix can also deliver ADNS peptides. ADNS peptides may be administered extracerebrally in a form that has been modified chemically or packaged so that it passes the blood-brain barrier, or it may be administered in connection with one or more agents capable of promoting penetration ADNS peptide across the barrier. For example, a conjugate of NGF and monoclonal anti-transferrin receptor antibodies has been shown to be transported to the brain via binding to transferrin receptors. To achieve the desired dose of ADNS peptide, repeated daily or less frequent injections may be administered, or truncated ADNS peptide may be infused continuously or periodically from a constant- or programmable-flow implanted pump. The frequency of dosing will depend on the pharmacokinetic parameters of ADNS peptide as formulated, and the route of administration.

Regardless of the manner of administration, the specific dose is typically calculated according to body weight or body surface area. For diseases involving the brain, the specific dose is typically calculated according to the approximate brain weight of the subject, which also may be estimated based on body weight or body surface area. Further refinement of the calculations necessary to determine the appropriate dosage for treatment involving each of the above mentioned formulations is routinely made by those of ordinary skill in the art, especially in light of the dosage information and assays disclosed herein. Appropriate dosages may be ascertained through use of the established assays for determining dosages utilized in conjunction with appropriate dose-response data. The final dosage regimen involved in a method of treating a specific condition will be determined by the attending physician, considering various factors which modify the action of drugs, e.g., the age, condition, body weight, sex and diet of the subject, the severity of any infection, time of administration and other clinical factors.

ADNS peptides of the present invention may also be employed, alone or in combination with other growth factors in the treatment of nerve disease. For example, ADNS peptides may be used in treating some forms of nerve disease in combination with nerve growth factor. In addition, other factors or other molecules, including chemical compositions, may be employed together with ADNS peptides. In the treatment of Parkinson's disease, it is contemplated that ADNS peptide be used by itself or in conjunction with the administration of Levodopa, wherein the ADNS peptide would enhance the production of endogenous dopamine and the neuronal uptake of the increased concentration of dopamine.

As stated above, it is also contemplated that additional neurotrophic or neuron nurturing factors will be useful or necessary to treat some neuronal cell populations or some types of injury or disease. Other factors that may be used in conjunction with ADNS peptides include, but are not limited to: mitogens such as insulin, insulin-like growth factors, epidermal growth factor, vasoactive growth factor, pituitary adenylate cyclase activating polypeptide, interferon and somatostatin; neurotrophic factors such as brain derived neurotrophic factor, neurotrophin-3, neurotrophin-4/5, neurotrophin-6, insulin-like growth factor, ciliary neurotrophic factor, acidic and basic fibroblast growth factors, fibroblast growth factor-5, transforming growth factor-.beta., cocaine-amphetamine regulated transcript (CART) and mature GDNF; and other growth factors such as epidermal growth factor, leukemia inhibitory factor, interleukins, interferon, and colony stimulating factors; as well as molecules and materials which are the functional equivalents to these factors.

It is envisioned that the continuous administration or sustained delivery of a ADNS peptide may be advantageous for a given treatment. While continuous administration may be accomplished via a mechanical means, such as with an infusion pump, it is contemplated that other modes of continuous or near continuous administration may be practiced. For example, chemical derivatization may result in sustained release forms of the protein which have the effect of continuous presence in the blood stream, in predictable amounts, based on a determined dosage regimen. Thus, ADNS peptides of the present invention include ADNS peptides derivatized to effectuate such continuous administration.

ADNS peptide cell therapy, e.g., intracerebral implantation of cells producing ADNS peptides, is also contemplated. This embodiment of the present invention may include implanting into subject's cells which are capable of synthesizing and secreting a biologically active form of the ADNS peptides of the present invention. Such ADNS peptide producing-cells may be cells which do not normally produce a neurotrophic factor but have been modified to produce ADNS peptides, or they could be cells whose ability to produce GDNF has been augmented by transformation with a polynucleotide suitable for the expression and secretion of ADNS peptides. In order to minimize a potential immunological reaction in subjects, it is preferred that the cells be of human origin.

Implanted cells may be encapsulated to avoid infiltration of the cells into brain tissue. Human or non-human animal cells may be implanted in subjects in biocompatible, semi-permeable polymeric enclosures or membranes to allow release of an ADNS peptide, but that prevent destruction of the cells by the subject's immune system or by other detrimental factors from the surrounding tissue. Alternatively, the subject's own cells, transformed ex vivo to produce ADNS peptides, could be implanted directly into the subject without such encapsulation.

The methodology for the membrane encapsulation of living cells is familiar to those of ordinary skill in the art, and the preparation of the encapsulated cells and their implantation in subjects may be accomplished. See for example, U.S. Pat. Nos. 4,892,538; 5,011,472; and 5,106,627, the disclosures of which are hereby incorporated by reference. A system for encapsulating living cells is also described in PCT Application WO 91/10425 of Aebischer et al., specifically incorporated herein by reference. See also, PCT Application WO 91/10470 of Aebischer et al.; Winn et al., *Exper. Neurol.*, 113:322-329, 1991; Aebischer et al., *Exper. Neurol.*, 111:269-275, 1991; and 35 Tresco et al., *ASAIO*, 38:17-23, 1992, the disclosures of which are hereby incorporated by reference.

ADNS peptide gene therapy in vivo is also envisioned, wherein a nucleic acid sequence encoding an ADNS peptide is introduced directly into the subject. For example, a nucleic acid sequence encoding an ADNS peptide is introduced into target cells via local injection of a nucleic acid construct with or without an appropriate delivery vector, such as an adeno-associated viral vector. Alternative viral vectors include, but are not limited to, retrovirus, adenovirus, herpes simplex virus and papilloma virus vectors. Physical transfer may be achieved in vivo by local injection of the desired nucleic acid construct or other appropriate delivery vector containing the desired nucleic acid sequence, liposome-mediated transfer, direct injection (naked DNA), receptor-mediated transfer (ligand-DNA complex), or microparticle bombardment (gene gun). It should be noted that the ADNS peptide formulations described herein may be used for veterinary as well as human applications and that the term "subject" should not be construed in a limiting manner. In the case of veterinary applications, the dosage ranges should be the same as specified above.

As a means of further characterizing the ADNS peptides of the present invention, antibodies can be developed which bind to the ADNS peptides. One of ordinary skill in the art can use well-known, published procedures to obtain monoclonal and polyclonal antibodies, or recombinant antibodies, which specifically recognize and bind to the various ADNS peptides of the present invention.

Other aspects and advantages of the present invention will be understood upon consideration of the following illustrative examples. The examples are not to be construed in any way as limiting the scope of this invention.

EXAMPLES

Example 1

BLAST Analysis

The three hypothetical precursor segments (RRERNRQAAAANPENSRGKGRR (SEQ ID NO: 5); FPLPAGKR (SEQ ID NO: 8); and KRPPEAPAEDRSLGRR (SEQ ID NO: 7); see FIG. 3) were subjected to BLAST searches for short, nearly identical sequences. RRERNRQAAAANPEN- SRGKGRR (SEQ ID NO: 15) is present in GDNF splice forms 1 and 2. There are some sequence variations by species, but consensus post-translational processing signals are maintained across species. FPLPAGKR (SEQ ID NO: 8) was found to be invariant in the available GDNF splice form 1 sequences, but does not occur in splice forms 2 and 3. KRPPEAPAEDRSLGRR (SEQ ID NO: 7) scored hits in splice form 1, but not in the other GDNF splice forms. There are some sequence variations by species, but consensus processing signals are maintained across species. Thus, these ADNS peptides are unique to mostly splice form 1 of GDNF and not other splice forms of the pre pro GDNF.

Example 2

Synthesis of ADNS Peptides

Three peptides, designated GER9263, GER9264, and GDR9265 (see Table 1, below) were synthesized by Keck Biotechnology Resource Laboratory, Yale University New Haven, Conn. Synthetic peptides can be made routinely up to 40 residues and often, depending on sequence, up to 70 residues by this facility. All peptides were separated and purified on a preparative C-18 or C-4 RP-HPLC system and delivered as a lyophilized material. Yields for normal peptides under 40 residues were "guaranteed" at 50 mg or more and at 90+% purity. Yields and purity are often higher, varying with the peptide sequence and length. All peptides made in the Keck facility at the 0.5 mmole scale are done by tBOC chemistry and at a single scale range (which generates a theoretical crude yield of 500-1,000 mg for a 10-20 mer respectively). The purified peptides were characterized by analytical RP-HPLC, amino acid analysis, and FAB mass spectroscopy.

TABLE 1

ADNS peptides

| Peptide | Sequence |
|---|---|
| GER9263 | ERNRQAAAANPENSRGK-amide (SEQ ID NO: 2) |
| GER9264 | FPLPA-amide (SEQ ID NO: 3) |
| GDR9265 | PPEAPAEDRSL-amide (SEQ ID NO: 4) |

Example 3

Dopaminergic Activity of ADNS Peptides in Fischer 344 Rats

Experiments were performed to test the effects of the three ADNS peptides (GER9263, GER9264, and GDR9265) on dopaminergic activity in normal young adult male Fischer 344 rats. The peptides were combined in a 1:1:1 ratio. There were three test groups with six animals per group: vehicle (citrate buffer), vehicle plus 30 µg peptide mixture, and vehicle plus 100 µg peptide mixture. The vehicle or vehicle plus peptide solutions were steriotaxically injected in equal portions into two sites each in the right substantia nigra.

One month after drug administration, the basal levels of dopamine and dopamine metabolites were measured by microdialysis in the right striatum. Potassium and amphetamine evoked release of dopamine were also evaluated.

Figure 5:
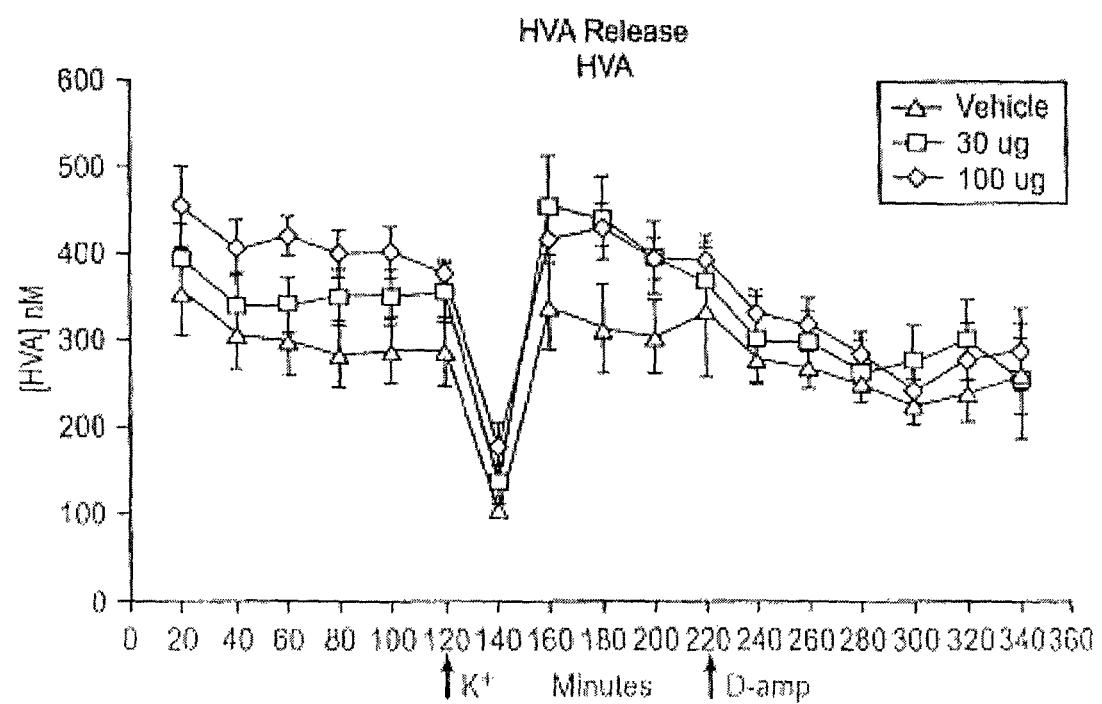
FIG. 5 depicts the increase in major metabolites of dopamine in Fischer 344 rats treated with ADNS peptides.

While basal levels of dopamine were not significantly altered in the striatum, average $K^+$-evoked release of dopamine increased by over 50% (FIG. 4). Average amphetamine-evoked release was more variable, but ranged from about 30% for 100 µg to about 45% for 30 µg. While basal dopamine levels were about the same in all three groups, basal metabolite levels were elevated. As shown in FIG. 5, the major metabolites 3,4-Dihydroxy-Phenylacetic Acid (DOPAC) and Homovanillic Acid (HVA) were increased by about 40% (DOPAC) and 20-40% (HVA), depending upon the dose.

Example 4

Figure 6:
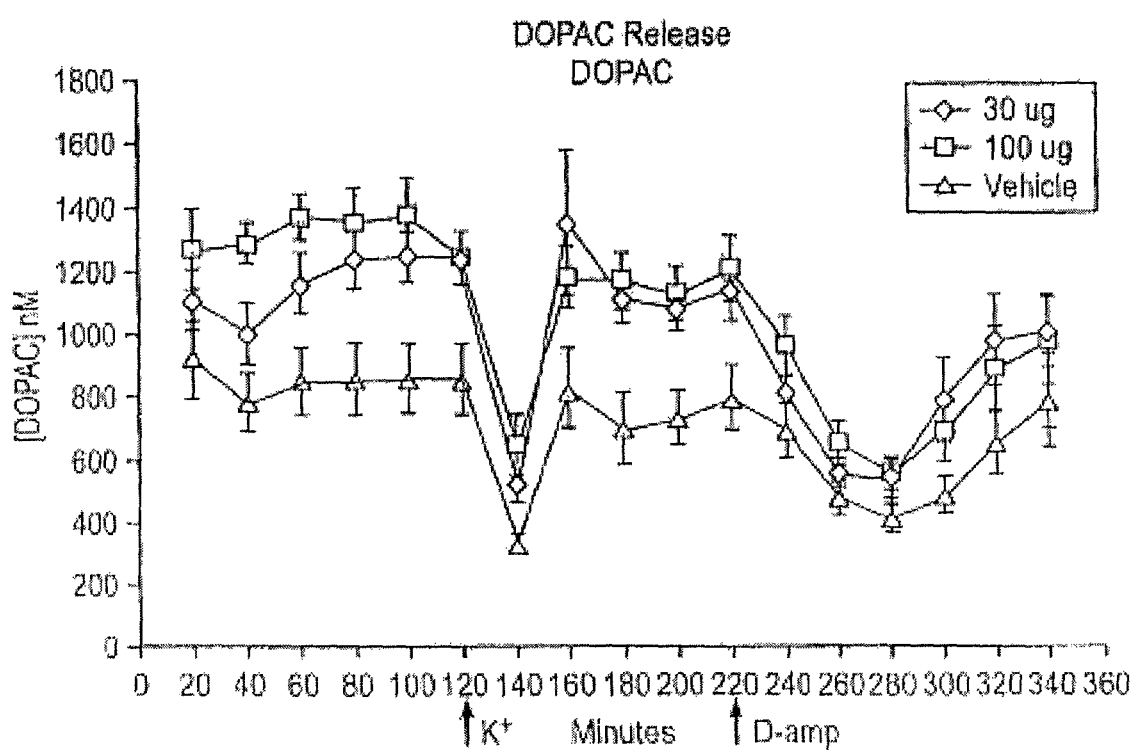
FIG. 6 depicts the increased survival of dopamine neurons in cell cultures treated with ADNS peptides.

Dopaminergic Activity of ADNS Peptides in Cell Cultures of Rat Midbrain Dopamine Neurons To further characterize the bioactivity of the peptides, blinded samples were sent to Dr. Michael Zigmond at the University of Pittsburgh for testing in cultures of newborn rat midbrain dopamine neurons. Peptide mixture samples (GER9263, GER9264, and GDR9265 combined in a 1:1:1 ratio) were compared to citrate buffer alone, two different lots of GDNF, and Neurturin (FIG. 6). Both lots of GDNF and the 100 ng/ml ADNS peptide mixture exerted about the same effects in dopamine neuron survival, increasing survival by about 25-30% over vehicle levels. The peptide mixture at a concentration of 50 ng/ml promoted an increase in survival of around 10%, approximately the same effect as 100 ng/ml Neurturin, a trophic factor that is closely related to GDNF.

Example 5

ADNS Peptides and Response to CNS Delivery in an Aged Rhesus Monkey

A study was performed demonstrating that a mixture of three ADNS peptides (GER9263, GER9264, and GDR9265 combined in a 1:1:1 ratio) exerts pharmacological effects on CNS nigral dopamine neurons in an aged rhesus monkey similar to those produced by GDNF. Marked increases of 68-125% in stimulus-evoked dopamine release were measured in the putamen by in vivo microdialysis. Motor speed, as measured in fine motor hand movements, increased by up to 58%, into the range of young adult monkeys. General body movements increase by 38%, indicating much higher activity levels. The effects from unilateral treatment were long-lasting (for at least one month) and bilateral, similar to those resulting from GDNF treatment. Histopathological analysis of the injection sites in the substantia nigra revealed only mild, circumscribed pathology from the peptide injections. The pharmacological effects of ADNS peptides on upregulating nigrostriatal dopamine system functions are extraordinary and suggest their potential therapeutic use for the treatment of Parkinson's disease and age-associated movement dysfunctions.

The ADNS peptides tested in this Example are three amidated peptides predicted to exert potent biological effects similar to those of Glial Cell Line-Derived Neurotrophic Factor (GDNF). The effects of GDNF on CNS dopamine neurons fall generally into three categories: pharmacological upregulation of dopaminergic activity, neuronal regeneration and neuroprotection. This study was designed to assess the pharmacological effects of ADNS peptides on substantia nigra dopamine neurons in the nonhuman primate brain. It was previously shown that CNS delivery of GDNF increases stimulus-evoked dopamine release in aged rhesus monkeys (Grondin et al., 2003). In addition, behavioral correlates of increased dopaminergic activity were recorded in these animals, improved motor functions and increased motor speed. The present study was a case report on one aged monkey that received a 100 μg injection of ADNS peptides into the substantia nigra of the brain and was followed for 30 days. Motor speed was measured weekly using an automated movement analysis panel (MAP) and EthoVision, a video tracking program. Movement features were rated weekly using a nonhuman primate clinical rating scale (Zhang, Z. et al., "*Motor slowing and parkinsonian signs in aging rhesus monkeys mirror human aging.*", *J Gerontology: Biol. Sci.* 55A: δ473-8480, (2000)). Stimulus-evoked dopamine release was analyzed by microdialysis at the 30 day time point. The animal was then euthanized and the brain recovered for histopathological analysis.

Methods Used for Studying ADNS Peptides

Animal:

A thirty-four year old female rhesus monkey (ID# NJ05) weighing 7 kg was used. The animal was diagnosed as having an inoperable mammary tumor, with the attending veterinarian suggesting that the monkey be placed in a terminal study and euthanized for humanitarian reasons. The animal was maintained on a 12-hour light/12-hour dark cycle and housed individually in a cage measuring 9 square feet, with an elevated perch, front access doors and side rear access doors connecting the housing cage to an adjacent activity module. The diet consisted of certified primate biscuits given in the morning (7:30 AM), and supplemented daily in the afternoon (1:30 PM) with fresh fruit or vegetables. Water was available ad libitum.

All procedures were conducted in the Laboratory Animal Facilities of the University of Kentucky, which are fully accredited by the Association for Assessment and Accreditation of Laboratory Animal Care. Veterinarians skilled in the health care and maintenance of nonhuman primates supervised all animal care.

MRI Imaging:

Magnetic resonance images (MRI) were obtained on a 10.5 T clinical imager (Siemens Magnetom Vision) using a standard cross polarized extremity coil. After being sedated with ketamine hydrochloride (~20 mg/kg; i.m.) plus atropine sulfate (~0.04 mg/kg; i.m.), the animal was anesthetized with sodium pentobarbital (~10 mg/kg; i.v.) and imaged to provide stereotaxic coordinates for peptide delivery. The animal's head was positioned in the extremity coil using an MRI compatible stereotaxic head frame. This frame kept the animal's head level and immobilized at the center of the radio frequency coil using ear and mouth bars. An initial set of coordinates was taken using the earbars, toothbar and a zeroing bar targeted to the gum line between the two upper middle incisors to allow replication any time the animal was replaced in the stereotaxic apparatus.

The coil/frame assembly was then positioned to place the animal's head at magnet isocenter. Sets of T1-weighted 3D-FLASH images were collected for determination of the brain coordinates (TR/TE=22/9 ms; FA=35°; FOV=96×96× 90 mm; Matrix=128×128×90; Nacq=2; TA=6 min 48 sec). All images were acquired as coronal slices relative to the brain. Antero-posterior, lateral and vertical coordinates for stereotaxic surgery were derived from the T1-weighted coronal brain images. The interaural line was identified on the scans by modified earbars containing Vitamin E. This provided a precise reference-point, which allowed for anteroposterior measurements to the target. Lateral measurements were determined by measuring the distance from the sagittal sinus/third ventricle to the target site. Vertical measurements were determined from the surface of the brain to the target at the lateral coordinate.

Surgery:

Following sedation with ketamine hydrochloride (~20 mg/kg; i.m.) plus atropine sulfate (~0.04 mg/kg; i.m.), the animal was intubated via the orotracheal method and intravenous lines secured. Then, the animal was anesthetized with isoflurane (1-3%) and placed in an MRI compatible Kopf stereotaxic apparatus in a ventral-lateral position as per the coordinates previously (see Anatomical MRI above). The animal was maintained on a heated blanket and had cardiac and respiratory parameters monitored during the procedure, which was carried out using sterile field conditions. Coordinates for peptide injections were determined by MRI prior to the surgery as described above. After being shaved, the scalp area was cleaned using antiseptic procedures with sterile 4×4 sponges soaked in Betadine® surgical scrub followed by 70% isopropyl alcohol. This procedure was repeated. After the alcohol dried, Betadine® prep was applied and the animal was covered with sterile drapes. Then, an incision was made through the scalp and the skin and muscles overlying the skull were reflected. Small holes were drilled in the skull directly over the target area. The overlying meninges were removed to expose the surface of the brain.

A 1.0 mg/ml concentration of the three-peptide mixture in citrate buffer was used. It was sterilized by filtration prior to injection Using MRI-guided procedures, a 27 G needle coupled to a Hamilton syringe containing 100 μl (i.e. 100 μg) of the peptide mixture was lowered in the right rostral SNc (AP: 11, L: 5, DV: 30 from surface of the brain). A volume of 50 μl was delivered using a nanopump at a rate of 1 μl/min. This was followed by a 20 min waiting period before retracting the needle out of the brain (1 mm/min). The needle/syringe assembly was then moved 1 mm caudally and 0.5 mm laterally and lowered into the more caudal SNc (AP: 10, L: 5.5, DV: 29 from surface of the brain). This was followed by a 20 min waiting period before retracting the needle out of the brain (1 mm/min). After completion of the injections, the scalp incision was sutured over the exposed areas per normal procedures and the animal was given an analgesic (buprenorphine, 0.01 mg/kg, i.m.). Vital signs were monitored until the animal awakened, at which point the animal was covered with warm blankets and taken back to its cage and monitored until it was ambulatory.

Behavioral Tests:

To assess changes in motor functions, the animal was videotaped prior to injecting the peptide mixture, and weekly after the injection for four weeks. The videotaping cage measured 28 in W×32 in H×32 in D, had a white background wall and a clear Lexan window permitting videotaping. The videotaping cage was illuminated by two 48 in-long fluorescent lights located 30 in above. Water (via a cage attached bottle) was available ad libitum throughout the session. The animal was fed fruit or vegetables after completion of data acquisition and upon return to its home cage.

Beginning at 1 PM, a technician entered the room and placed small food items (e.g. gummy bears) on the ledge of the cage to elicit the animal to stand-up and reach out for the food. Then, the animal was videotaped for 30 minutes with no one in the room. Following this 30-minute videotaping period, the technician re-entered the room, stopped recording and attached a non-wired version of the monkey Movement Analysis Panel (MAP, see below) to the doorway of the cage for a hand retrieval test. Five to six preferred small food items (e.g. miniature marshmallows) were placed on each side of the panel. The animals was given 10 minutes (default time) to retrieve the food items, at which point the tester re-entered the room and stopped recording. This portion of the session was videotaped, with a focus on the hands. Starting at 2 PM, the same procedures described above were repeated. At the end of the testing session, the animal was returned to its home cage.

As described above, standardized videotaping procedures were conducted pre- and post-treatment. Behavioral parameters associated with motor function were scored from coded videotapes from 0 (normal) to 3 (severe disability) in the following categories: rigidity, bradykinesia, posture, balance, tremor, and hand dexterity (see Zhang et al., 2000). Rigidity is defined as a decrease in limb extension and/or use. Motor dysfunctions were rated in half-point increments by an experienced rater.

Distance traveled (cm) was quantified from 8-mm videotapes (SONY P6-120 MPL) using a commercially available video tracking system EthoVision Pro (version 2.3, Noldus Information Technology, Asheville, N.C.) coupled to a SONY Digital 8 video cassette recorder. This system runs on a Pentium based computer with a frame grabber card (PICOLO, Belgium), so that the analog video signal coming from the video cassette recorder is digitized and transferred to the computer. A window on the computer screen directly displays the video image, and the boundaries within which tracking took place were defined by accurately tracing the outline of the cage in the video image, in addition, two zones were outlined, so that the overall activity measured in the entire cage could be analyzed in terms of vertical (top half) or horizontal (bottom half) activity. As described above, the animal was videotaped for 60-minute periods, pre- and post-treatment, and the video tracks were analyzed at a rate of 6-sample/sec. For every sample, the cage was scanned and the position of the tracked animal was determined by using a gray scale detection method (brightness). This entails calibrating the software to distinguish the dark-colored animal from the background, which is then defined as all other pixels. The back wall of the cage was painted white to provide a background with a maximum degree of contrast with the dark-colored primate. This automated method relies on determining the position of the center of mass of the animal in the cage, and the resultant x-y coordinates extracted as a function of time are used for calculating the movement pattern during the observation period. These coordinates were subsequently related to actual spatial measures by calibrating the software to the dimension (width) of the cage, the distance traveled by the animal were calculated in centimeters instead of pixels.

Movement Analysis Panel (MAP):

In addition, fine/hand motor movement times in retrieving food items from a platform level placed in a receptacle chamber were measured using an automated clear Lexan MAP attached to the door opening of the home cage (see Gash, D. M. et al. "An automated movement analysis panel for upper limb motor functions in rhesus monkeys and humans", J. Neurosci Methods 89:111-117, (1999) and Zhang et al., 2000). The receptacle chamber is divided into left and right halves, and is accessible on each side through two portals (armhole portal and receptacle portal). Movement times were measured by arrays of three photodiodes around each portal that automatically relayed to the computer when one or more beams were broken by passage of the monkey's arm/hand. Testing was conducted in the afternoon, prior to injecting the peptide mixture, and weekly thereafter for four weeks. Fresh fruit and vegetables were given to the animal after completion of the testing session. A day's testing session consisted of twelve trials, six on each side alternating between the right and left hand.

Microdialysis Studies:

The animal underwent bilateral putamenal microdialysis one month post ADNS peptide injection. Using the method described below, in vivo microdialysis procedures had also been conducted previously in the right striatum of the same animal (date: Feb. 10, 2004; coordinates: AP: 20.5 mm, L: 10.2 mm, DV from cortex: 21 mm).

Following normal MRI-guided stereotactic procedures (see Surgical procedures for ADNS peptide injection), custom-made CMA/11 dialysis probes with a membrane length of 3 mm and diameter of 0.24 mm (CMA Microdialysis, North Chelmsford, Mass.) were positioned (1 mm/min) bilaterally in the putamen (AP: 20 mm, L: 10.5 mm, DV from cortex: 20 mm). Probes were perfused continuously at a rate of 1.2 µl/min with artificial cerebrospinal fluid using a computerized multisyringe pump (World Precision Instruments). Microdialysate fractions were collected at 30 min intervals.

Following a 1-hour application of artificial cerebrospinal fluid to collect baseline fractions, excess potassium (100 mM KCl, 47.7 mM NaCl) was then included in the perfusate for a single 30-min fraction (t0-t30). Two hours later 250 µM amphetamine was included in the perfusate for a single 30-min fraction (t1-t150). Three additional fractions were collected after discontinuing amphetamine administration (t180-t240). The incision was then closed as per normal surgical procedures. Microdialysate fractions were analyzed using standard high performance liquid chromatography procedures coupled with electrochemical detection.

Tissue Collection Procedures:

Tissue biopsies were collected for possible future use. At the end of the dialysis session, the animal was immediately euthanized. The deeply anesthetized animal (2 ml pentobarbital, i.v.) was transcardially perfused with heparinized ice-cold saline (6 L). Then, the brain was removed quickly, and dropped into a container of cold saline, which was placed on wet ice and taken back to the laboratory. Using an ice-cold mold, the brain was sectioned into 4-mm coronal slabs, rostral of the midbrain.

Multiple tissue punches were taken bilaterally from frozen 4-mm thick coronal tissue sections using a 14 G biopsy needle in the caudate nucleus (n=18 per side, tissue slabs #3, #4 and #5), putamen (n=18 per side, tissue slabs #4, #5, #6), nucleus accumbens (n=7 per side, tissue slabs #3 and #4) and globus pallidus (n=5 per side, tissue slabs #6). Separate needles were used for the right and left (green tape) hemisphere. All punches were rapidly transferred to pre-weighed storage tubes, weighed once more, and stored at −80° C. Pictures of the punched slabs were taken to document the punching pattern, and then they were stored at −80° C.

The midbrain was taken out as a block, which included the cerebellum, and post-fixed for quantitative immunocytochemistry of substantia nigra dopamine neurons and TH+ processes. To do so, the midbrain was immediately immersed in 4% paraformaldehyde in 0.1 M phosphate buffer (pH 7.4) at 4° C. for three days and transferred to 15% sucrose solution until saturated for sectioning. Then, a series of 40 µm-thick coronal sections were cut on a frozen sliding microtome. One out of every 12th adjacent sections was processed for cresyl violet (Nissl) and hemotoxylin and eosin (H & E) staining. Also, 1/12th adjacent sections were processed for the following staining: a) 1:1000 mouse anti-glia fibrillary acidic protein (GFAP) antibody for astrocytes, b) 1:200 mouse anti-HLA-DR antibody for reactive microglia, and c) 1:1000 mouse anti-tyrosine hydroxylase (TH) antibody for dopaminergic neurons (see Ai et al., 2003).

Effects of ADNS Peptides on an Aged Rhesus Money

The animal recovered without problems from peptide delivery into the right substantia nigra. No clinically observable abnormal behaviors (e.g. auto-mutilation, stereotypic movements, dyskinesia, vomiting) were noted throughout the 30-day study.

As described above, standardized videotaping procedures were conducted pre- and post-treatment to assess changes in motor functions from coded videotapes. Prior to injecting the three-peptide mixture into the right substantia nigra, the animal was given a cumulative score of 3.25 points on the rating scale (See Table 2). Although the effect was variable, this score improved (the lower the score, the better the movement functions) by over 30% (i.e. 1 point) by the fourth week of the study. Similarly, distance traveled (cm) measured over weekly 60-minute periods using the automated video-tracking system (EthoVision) improved up to 38% by the fourth week post treatment versus baseline locomotor activity (from 7064 cm to 9780 cm). Last but not least, MAP performance times for left hand motor were 56% faster by week four post peptide treatment (from 0.81 sec to 0.36 sec). Right hand performance times were already faster than the left pre-peptide treatment. They further improved in the 4 weeks post-treatment, with performance times 14% faster (from 0.36 sec to 0.31 sec).

Figure 7A:
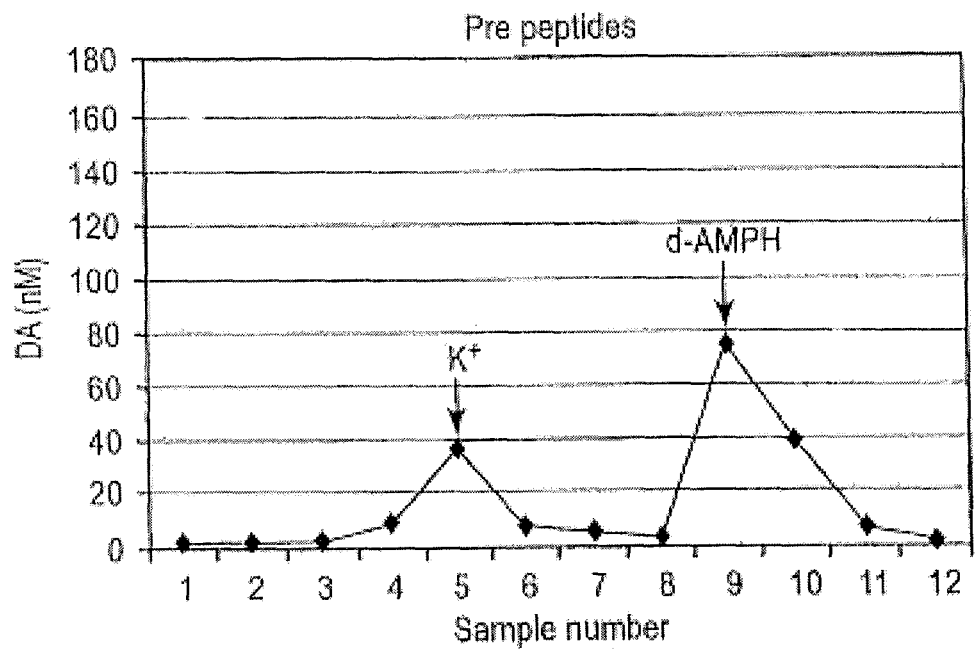
FIGS. 7A and B depict the results of in vivo microdialysis used to investigate the dynamics of dopamine release in the basal ganglia of the right putamen following treatment with ADNS peptides.
Figure 7B:
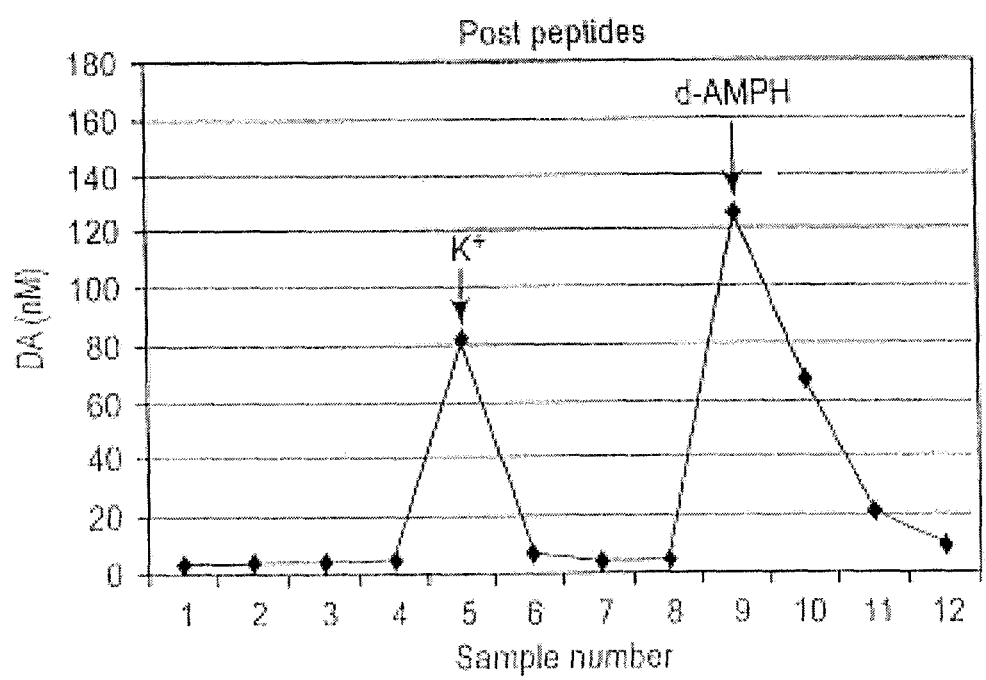
Figure 8A:
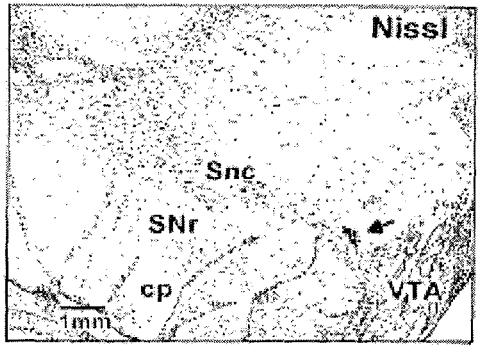
FIGS. 8A-F depict the histopathological response to the injection of ADNS peptides in the nigral region using standard histochemical techniques.
Figure 8D:
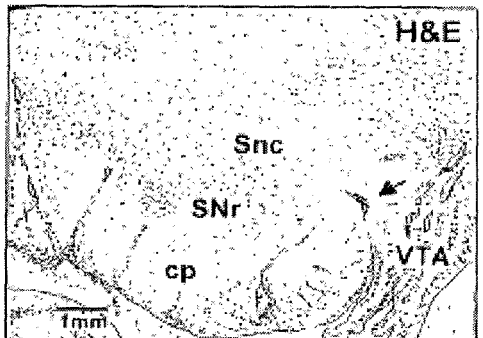
Figure 8B:
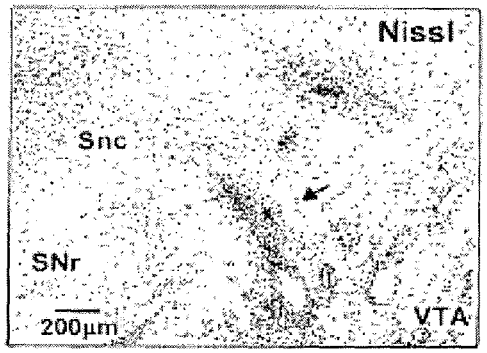
Figure 8E:
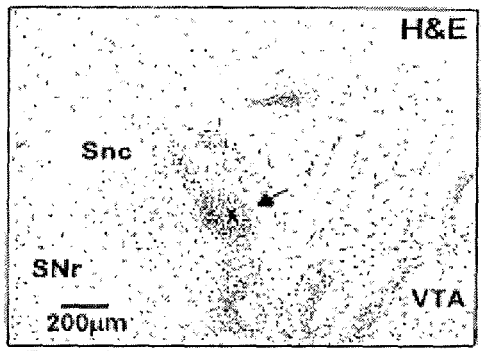
Figure 8C:
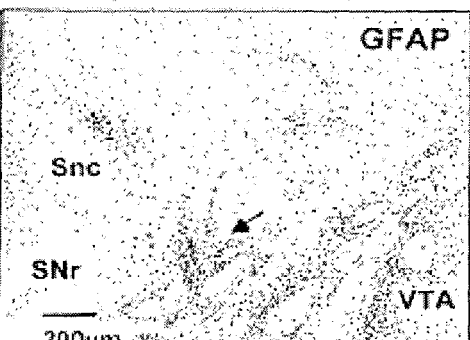
Figure 8F:
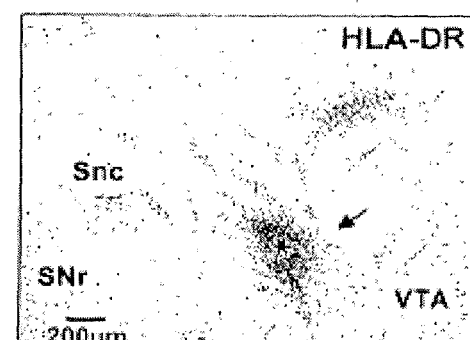
Figure 9A:
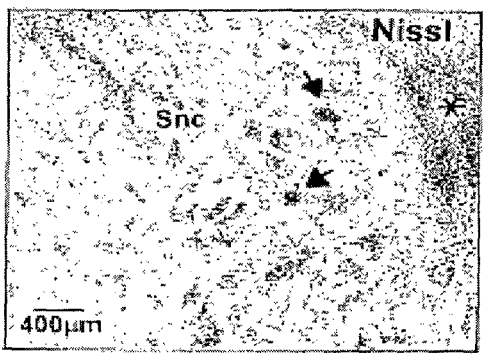
FIGS. 9A-D depict a series of photomicrographs evaluating the substantia nigra compacta (SNc) containing the population of dopamine neurons that degenerates in Parkinson's disease after treatment with ADNS peptides.
Figure 9B:
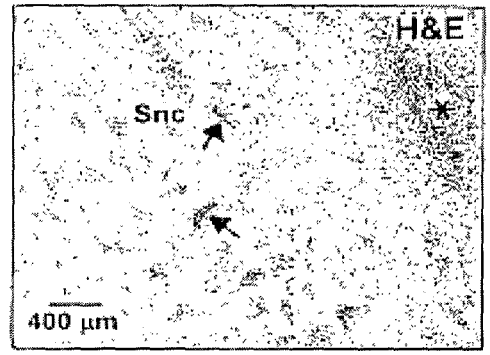
Figure 9C:
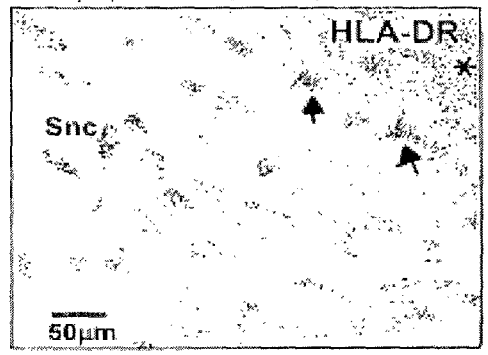
Figure 9D:
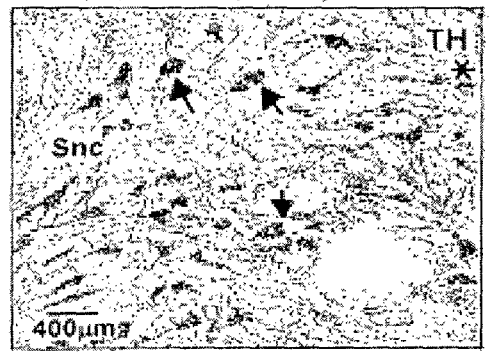

In vivo microdialysis was used to investigate the dynamics of dopamine release in the basal ganglia. Measurements were carried out in the right putamen four weeks post peptide treatment (see FIGS. 7A and B). In particular, FIG. 7 shows the results of potassium (K+) and d-amphetamine (d-AMPH) evoked release of dopamine measured in the right putamen of NJ05 using microdialysis to collect samples for neurochemical analysis. FIG. 7A shows the first recordings made Feb. 10, 2004, several years prior to the ADNS peptide study. In aging monkeys, dopamine evoked release of dopamine to K+ and d-AMPH normally decreases with increasing age. FIG. 7B shows the second set of recordings made thirty days after ADNS peptide injections into the right substantia nigra on Apr. 27, 2006. K+ evoked release was increased from the 2004 reading from 36.5 nM to 82 nM. D-AMPH evoked release of dopamine increased from 74 nM to 125 nM after ADNS peptide administration. Thus, in comparison to measurements recorded under similar conditions two years earlier in the same animal, potassium-evoked overflow of dopamine was increased by 125% at 30 days post ADNS peptide administration (from 36.5 nM to 82 nM). Similarly, amphetamine-induced overflow of dopamine was increased by 68% compared to measurements recorded two years earlier (from 74 nM to 125 nM).

Basal levels of dopamine and dopamine metabolites in the striatum were determined from measurements in the microdialysates prior to potassium and amphetamine stimulation. Basal dialysate levels of dopamine and HVA showed small changes from the baseline levels two years earlier (Table 2). However, basal levels of extracellular DOPAC were increased by 230% at thirty days post peptide injection compared to the earlier baseline measures (Table 3).

The histopathological response to the injection of peptides in the nigral region was mild (see FIGS. 8 and 9). In FIG. 8, one of the injection sites (arrow) is shown using standard histochemical techniques for Nissl staining and hematoxylin and eosin (H & E) staining Immunostaining was conducted to assess the response of astrocytes (GFAP positive cells) and microglia (HLA-DR positive cells) to the injections. In FIGS. 8A and B, this injection site (arrow) was just dorsal to the substantia nigra, pars compacta (SNc). While there is an evident response at the injection site and a smaller satellite area (*) of reactivity dorsal to the main area, the injury response is very circumscribed. FIG. 8C shows that reactive astrocytosis, as assessed by GFAP positive reactivity around the needle track, is minimal, approximately that expected from a needle tract injury alone. In FIGS. 8D and E, the injury response appears similar using H & E to that seen with Nissl. The injury response is localized and does not seem to involve adjacent cells. Reactive microglia (HLA-DR+cells) are a prominent constituent of the injury response (arrow and *, FIG. 8F). (In FIG. 8, Cerebral peduncle=CP; Substantia nigra reticulatia=SNr; Ventral Tegmental Area=VTA. Scale bars are included in each photomicrograph.) The injection site showed reactive cells in an area about 200 μm wide by 400 μm long in Nissl-stained and H & E-stained sections (FIGS. 8 A, B, D and E). The response consisted of activated microglia (HLA-DR positive cells, FIG. 8F). The absence of pronounced GFAP immunostaining (FIG. 8) indicated that the injection did not stimulate a glial reaction.

The substantia nigra pars compacta (SNc) containing the population of dopamine neurons that degenerates in Parkinson's disease is evaluated in the series of photomicrographs set forth in FIG. 9. In FIG. 9A, Nissl-rich neurons (arrowheads) adjacent to the peptide injection site (*) appear normal with prominent nuclei evident in the nucleus of some cells. Nissl staining corresponds to the presence of rough endoplasmic reticulum in the cytoplasm and indicates cells actively synthesizing protein. The H & E stained section in FIG. 9B also shows neurons with normal features (arrowheads) adjacent to the injection site (*). FIG. 9C shows that there are only a few scattered activated microglia (arrowheads showing HLA-DR positive cells) in the SNc. Large numbers would indicate ongoing pathological processes. Tyrosine hydroxylase (TH) is the rate-limiting enzyme in dopamine synthesis. The TH positive cells shown in FIG. 9D are dopamine neurons. Their size and exuberant expression of TH positive processes are indicative of healthy, active cells. Scale bars are included in each photomicrograph. Dopamine neurons in the substantia nigra appeared to be normal (FIG. 9). Tyrosine hydroxylase immunostaining (FIG. 9D) revealed large dopamine neuron perikarya (cell bodies) with extensive neuritic processes. Along with the Nissl and H & E stained sections (FIGS. 9 A and B), the nigral cells showed features characteristic of healthy neurons. A few activated microglia (HLA-DR positive cells, FIG. 9C) were present in the nigral region, a typical feature of this brain region in healthy aged monkeys. Large numbers of activated microglia would be indicative of an ongoing disease process.

The subject in this study was a very old rhesus monkey, 34 years old. One year for a rhesus monkey is roughly equivalent to three years of human life, making this animal equivalent to a 100 year old person. The monkey was used in this study because it had a terminal disease, mammary cancer. The closest comparable monkeys in an earlier study treated with GDNF were 22-24 years old (Grondin et al., 2003). They received infusions of GDNF into the brain for 24 weeks while NJO5 had a single injection of an ADNS peptide mixture and was monitored for one month. Despite the differences, many of the responses were comparable to those seen to GDNF. NJO5 motor performance times on the MAP improved within four weeks on both the right (14%) and left (56%) sides. The improved motor speeds approached the speeds of aged monkeys receiving GDNF and those of normal young adult animals. Consistent with increased motor speed, general locomotor activity was increased by 38% for four weeks of treatment in NJO5. There were neurochemical changes in NJO5's brain along with the behavioral improvements. Both potassium- and amphetamine-evoked release were increased (125% and 68%, respectively) in the putamen in comparison to pre-treatment levels. This was similar to the increased evoked release of dopamine in response to the same stimulants in aged rhesus monkeys treated with GDNF (Grondin et al., 2003). Basal dialysate levels of dopamine, HVA and DOPAC showed high variability, but were not significantly changed in aged GDNF recipients. NJO5's basal dopamine and dopamine metabolite levels were in the same range as the GDNF and vehicle-treated old animals. The only dramatic change seen in this animal was in DOPAC levels, which increased over three-fold post ADNS peptide treatment. The significance of this response is that it reflects higher levels of dopamine metabolism in the striatum.

Histopathology was much less extensive than the damage in the same region from the infusion of GDNF (see Gash, D. M. et al., "*Trophic factor distribution predicts functional recovery in parkinsonian monkeys*", *Ann Neurol* 58(2):224-33 (2005)). The dopamine neurons in the substantia nigra appeared healthy, with numerous neuritic processes.

TABLE 2

Changes in motor functions post ADNS peptides delivery into the right *substantia nigra*. The reduction in the disability score means that the motor functions such as walking and balance were improving. The locomotor activity level increases by week four also reflect that the animal was increasing the time and distance in walking. The Movement Analysis Panel (MAP) scores demonstrate much faster hand fine motor movements by week 4 after treatment.

| Treatment | Disability Score (pts)/% baseline | Locomotor Activity (cm)/% baseline | Left Map Times (sec)/% baseline | Right MAP times (sec)/% baseline |
|---|---|---|---|---|
| Baseline | 3.25 | 7064 | 0.81 | 0.36 |
| Week 1 | 2.00/−38% | 8422/+19% | 0.86/+6% | 0.45/+25% |
| Week 2 | 2.00/−38% | 7136/+1% | 1.09/+35% | 0.39/+8% |
| Week 3 | 2.50/−23% | 6368/−10% | 0.75/−7% | 0.34/−6% |
| Week 4 | 2.25/−31% | 9780/+38% | 0.36/−56% | 0.31/−14% |

TABLE 3

Changes in basal dialysate levels of dopamine and dopamine metabolites in the right putamen, 30 days post ADNS peptide delivery into the right *substantia nigra*. The large increase in levels of the dopamine metabolite DOPAC indicate increase dopaminergic activity. As the enzyme (monoamine oxidase B) for metabolizing dopamine to DOPAC is on the outer membrane of mitochondria, it also reflects either more active mitochondria and increased numbers of mitochondria.

| Hemisphere | Dopamine (nM) | HVA (nM) | DOPAC (nM) |
|---|---|---|---|
| Pre-peptides | 5.6 | 5033 | 127 |
| Post-peptides | 4.9 | 4191 | 419 |

Example 6

Materials and Methods

The following materials and methods were used in the following examples.

Materials:

Unless otherwise stated, all cell reagents and assays were purchased from Invitrogen. All other materials and chemicals are reagent grade.

DNSP-17 (GER 9263), DNSP-5 (GER 9264), DNSP-11 (GER 9265), and Biotinylated DNSP-11: DNSP-17 (sequence: ERNRQAAAANPENSRGK-amide (SEQ ID NO: 2)), DNSP-5 (sequence: FPLPA-amide (SEQ ID NO: 3)): DNSP-11 (sequence: PPEAPAEDRSL-amide (SEQ ID NO: 4)) and biotinylated DNSP-11 (bDNSP-11; sequence: biotin-PPEAPAEDRSL-amide (SEQ ID NO: 4)) were synthesized and RP-HPLC purified to >98% by AC Scientific (Duluth, Ga.) and the W. M. Keck Foundation Biotechnology Resource Laboratory at Yale University. Peptides were characterized for purity and correct sequence by MALDI-TOF LC-MS and Edman degradation. DNSP-11 was determined to be stable, in vitro, at a variety of experimentally relevant concentrations and temperatures, including 37° C. in sterile pH 5 citrate buffer for 31 days.

Tissue Preparation for DNSP-11 Staining in Substantia Nigra at Postnatal Day (PN10):

Tissue was prepared from SD pups. Brains were rinsed in Dulbecco's Phosphate Buffered Saline (DPBS, Gibco), and submerged in 4% paraformaldehyde pH 7.4 for 48 hours. Following submersion in 30% sucrose, brains were sectioned coronally (40 μm) and stored in cryoprotectant solution at −70° C. until processed for immunohistochemistry.

DNSP-11 Treatment of Mesencephalic Cells:

Timed pregnant SD rats (Harlan) were used to obtain the ventral mesencephalon from E14 fetuses. The dissected tissue was collected in cold Neurobasal™ medium and rinsed twice with cold Dulbecco's PBS. The cells were chemically (TrypLE®) and mechanically dissociated to yield a single cell suspension. The solution was centrifuged at 169 g for 6 minutes and the pellet was resuspended in Dulbecco's Modified Eagle Medium (DMEM). Cells were plated in a 25 μL micro-island at a density of 4000 cells/μL on poly-D-lysine coated 24-well plates (Sigma). Following adherence, cells were supplemented with warm Neurobasal™ media containing 2 mM glutamine, 1×$N_2$, and 100 units of penicillin/streptomycin. Neurotrophic compounds were added at each media addition, including initial plating and DIV 2. A dose response of the peptides (0.03 ng to 10 ng/mL) was added to a 24-well plate following media supplementation.

MN9D Cell Cultures:

The MN9D cell line has been described by Choi (1991) *Brain Res.* 552:67-76 and was a gift from Michael Zigmond. Cells were cultured in DMEM supplemented with 10% Fetal Bovine Serum (FBS, Hyclone), 50 U/mL penicillin and streptomycin. For experiments, the cells were plated on 24-well poly-D-lysine in DMEM with 1% (v/v) penicillin-streptomycin. The cells were grown at 37° C. in 5% $CO_2$.

Caspase-3 Activity Assay in MN9D Cells:

MN9D cells were plated to 100,000 cells/well. Cell cultures were exposed to DNSP-11 (1 ng/mL) or buffer for 1 hour prior to 15 min 100 μM 6-OHDA exposure. Caspase-3 activity was monitored after 3 hours by fluorescence (excitation/emission 496/520 nm) using the Enz Chek Caspase-3 kit. Protein levels of lysed cells were measured by BCA assay (BioRad) and normalized for every experiment. Data expressed as % control and repeated a minimum of 3 times.

Terminal dUTP Nick-End Labeling (TUNEL) Assay in MN9D Cells:

After treatment with DNSP-11, MN9D cells were fixed and labelled to assess degenerative nuclear changes as indicated by the extent of high-molecular weight DNA strand breaks. DNA fragmentation was detected by using steptavidin-horseradish peroxidise conjugate followed by the substrate diaminobenzidine (DAB) generating a colored precipitate. Ratios between apoptotic and total cells were determined (4 random fields/well; 4 wells/group). Experiments were repeated 3 times.

Double Fluorescent Immunostaining of DNSP-11:

Floating sections were pretreated with 0.2% $H_2O_2$ in potassium phosphate buffered saline (KPBS) for 10 minutes and blocked with 4% normal goat serum in KPBS for 1 hour. Then, sections were incubated overnight with both rabbit anti-hDNSP-11 antibody (1:2000, Alpha Diagnostic) and mouse anti-TH antibody (1:1000, Chemicon) in KPBS at 4° C. After washing with KPBS, the sections were incubated with Alexa-488 conjugated goat anti-rabbit IgG (1:500, Molecular Probes) and Alexa-568 conjugated goat anti-mouse IgG (1:500, Molecular Probes) for 3 hours. The sections were washed extensively and visualized with a Nikon fluorescence microscope.

Animals and Surgical Procedures for Normal and 6-OHDA-Lesioned Rats:

Fischer 344 (F344) rats were used for all experiments and maintained under a 12 hour light/dark cycle with food and water provided ad libitum. All procedures were approved by the University of Kentucky Institutional Animal Care and Use Committee following AAALACI guidelines.

Infusion Delivery of DNSP-11 or Vehicle:

Isoflurane anesthetized (1.5-2.5%) F344 rats received 5 µl of 6 µg/µL DNSP-11 solution or citrate buffer vehicle solution in a blinded manner. Treatment was delivered to the nigral cell bodies using the same stereotaxic coordinates and protocol for solution delivery as in studies of GDNF[13].

Reverse Microdialysis:

Reverse in vivo microdialysis was accomplished using methods and brain coordinates described by Hebert et al. (1996) *J. Pharmacol. Exper. Ther.* 279:1181-1190. CMA 11 microdialysis probes with a 4.0 mm membrane length and 6 kDa molecular weight cut-off were placed within the rat striatum.

Unilateral 6-OHDA Lesions:

The 6-OHDA solution was delivered to two injection sites along the medial forebrain bundle (MFB) using a protocol described by Lundblad et al. (2002) *Eur. J. Neurosci.* 15:120-132. Five weeks after the unilateral 6-OHDA MFB lesion procedure, animals were grouped based on apomorphine (0.05 mg/kg, s.c.)-induced rotational behaviour: Animals with >300 rotations per 60 minutes were selected. Lesioned animals received 5 µL of either a 20 µg/µL DNSP-11 solution or citrate buffer vehicle solution in a manner similar to infusion delivery in normal animals.

Neurochemical Content of Tissue:

Lesioned animals were euthanized 5 weeks after DNSP-11 or vehicle infusion. The brains were sliced into 1 mm thick sections. Tissue punches were taken from the striatum and the substantia nigra and they were weighed, quick frozen and stored at −70° C. until they were assayed by high performance liquid chromatography with electrochemical detection as described by Hall et al. (1989) *LC/GC-Mag Sep Sci* 7:258-265.

Apomorphine-Induced Rotational Behavior Testing:

Lesion severity was assessed prior to DNSP-11 treatment using apomorphine (0.05 mg/kg, s.c.)-induced rotational behavior. Beginning one week after DNSP-11 treatment, apomorphine-induced rotational behavior was monitored weekly for four weeks as described by Hoffer et al. (1994) *Neurosci Lett.* 182:107-111 (1994) and Hudson et al. (1993) *Brain Res.* 626:167-174 (1993).

DNSP-11 Pull-Down Analysis:

The F344 substantia nigra was homogenized in homogenization buffer (modified from York et al. (2005) *FASEB J.* 19: 1202-4 with 20 mM HEPES, pH 7.4) and cytosolic fraction (supernatant) collected after 30 minutes at 100,000 g. 50 µg of bDNSP-11 was incubated with fraction for 15 minutes on ice. Sample was added to streptavidin magnetic beads (New England Biolabs), pelleted, and washed four times in homogenization buffer. Bound proteins were eluted by Solubilization/Rehydration Solution (7M Urea, 2M Thiourea, 50 mM DTT, 4% CHAPS, 1% NP-40, 0.2% Carrier ampholytes, 0.0002% Bromophenol blue), and analyzed by 2D-PAGE and MALDI-TOF MS.

Example 7

Neurobiological Actions of DNSP-11

GDNF is endogenously produced as a pre-proprotein of 211 amino acids that is processed and secreted as a mature homodimer with a molecular weight of 32-42 kDa. The following examples illustrate the neurobiological actions of dopamine neuron stimulating peptide-11 (DNSP-11), an 11-mer peptide that has been independently predicted to be an endopeptidase cleavage product from the human GDNF prosequence (FIG. 10A).

Figures 10A, 10B:
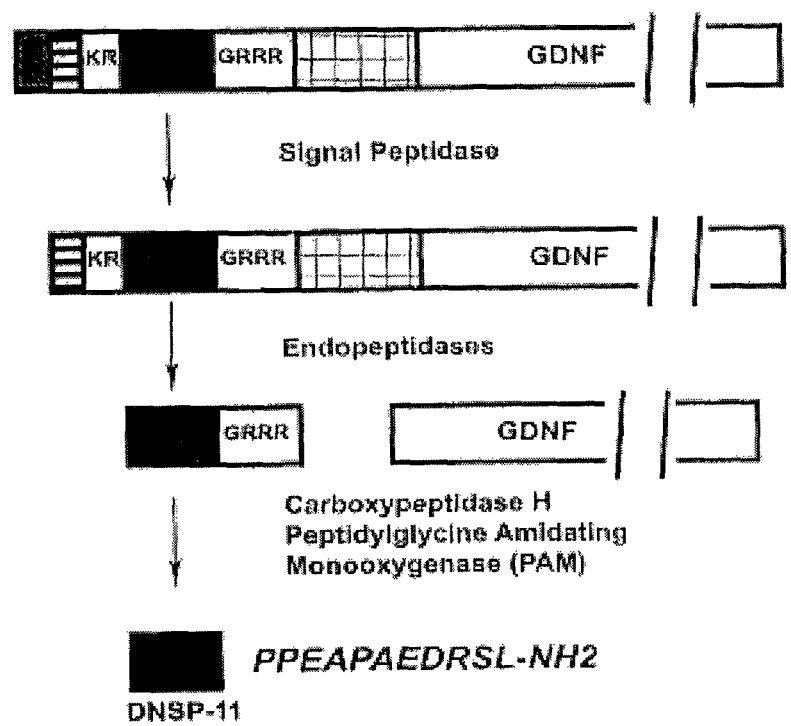
FIGS. 10A and B depict the sequence origin and homology of dopamine neuron stimulating peptide-11 (DNSP-11).

FIGS. 10A and 10B illustrate the sequence origin and homology of DNSP-11. DNSP-11 (filled) is an 11 amino acid sequence present in the proprotein region of the 211 amino acid human preproGDNF sequence. After cleavage of the pre-signal sequence (shaded), DNSP-11 is predicted to be cleaved from the proprotein at flanking dibasic cleavage sites by endopeptidases. Further predicted processing yields the C-terminal amidated peptide. The N-terminal (striped) and C-terminal (checkered) proprotein fragments and mature GDNF (open) protein are shown. The sequence figure is not drawn to scale to highlight the processing of DNSP-11. DNSP-11 (FIG. 10B) shows high sequence homology to the rat and mouse proGDNF sequences suggesting a conserved function.

In vivo expression of the DNSP-11 sequence in the substantia nigra of the ventral mesencephalon from SD pups at postnatal day 10 (PN10) was examined. Immunostaining for DNSP-11 in the mesencephalon of the SD pups indicated that the sequence is present endogenously in tyrosine hydroxylase positive (TH+) dopaminergic neurons of the substantia nigra at PN10 ns (yellow). The DNSP-11 sequence colocalized within dopaminergic cell bodies at PN10.

Figure 11A:
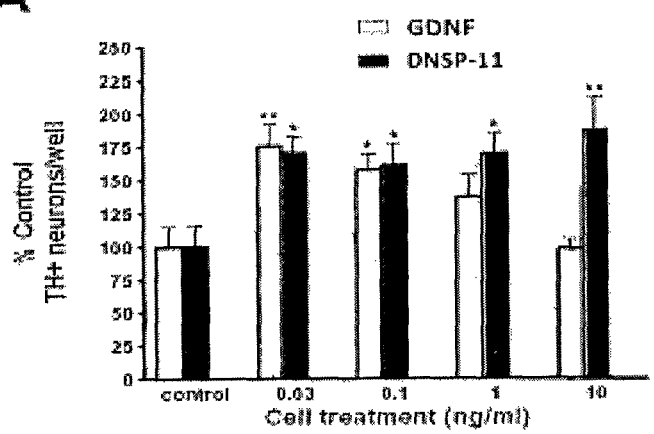
FIGS. 11A-D depict the neurotropic effects of DNSP-11 and GDNF on mesencephalic (A and B) and MN9D (C and D) dopaminergic cells.
Figure 11B:
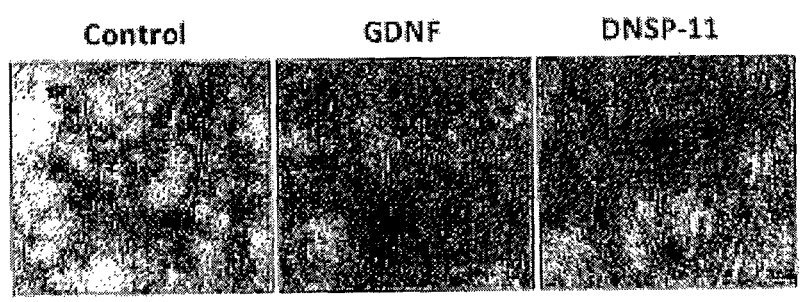

The neurotrophic effects of DNSP-11 were studied by comparing its effects to the well-known effects of GDNF on the maintenance of primary mesencephalic cell cultures from E14 SD rat embryos. E14 SD rat embryo primary dopaminergic neurons from the ventral mesencephalon were grown for 5 days in vitro and neurotrophic molecules were added at each media change, including initial plating and day 2. GDNF (FIG. 11A, open bars) and DNSP-11 (FIG. 11A, solid bars) were added at various concentrations (0.03, 0.1, 1.0 and 10 ng/ml; 10 mM citrate buffer+150 mM NaCl, pH 5) and were seen to significantly increase TH+ neuron counts (+SD; one-way ANOVA with Newman-Keuls post hoc analysis, *p<0.05 and ** p<0.01) Specifically, DNSP-11 increased cell survival 75% over citrate buffer control, as indicated by immunocytochemical staining of TH+ neurons 5 days in vitro (FIG. 11A). Furthermore, DNSP-11 significantly enhanced morphological changes consistent with a neurotrophic molecule including: neurite length, total number of branches, and increased total number of TH+ cells (Table 4; FIG. 11B). These effects were similar to those observed for GDNF in these cells, including an increase in the size of TH+ neurons, which was not observed for DNSP-11 (Table 4). Photographs in FIG. 11B of treated E14 primary dopaminergic neurons demonstrate that both GDNF and DNSP-11 treated cells (0.1 ng/ml) displayed enhanced cell survival, neurite length, and total number of branches.

In Table 1, cell survival and morphological parameters were quantified for control (citrate buffer) and experimental (0.1 ng/ml GDNF or 0.1 ng/ml DNSP-11) conditions. For morphology, five fields per well (minimum of 15 cells/field; 3-4 independent experiments) were photographed at 20× magnification and quantified using a Bioquant Image Analysis System. DNSP-11 increased cell survival and morphological parameters comparable to GDNF, including combined neurite length and total branches. Soma size was not increased by the addition of DNSP-11. A one-way ANOVA was used to test for significance among groups, followed by a Newman-Keuls post hoc analysis. Significance between control and experimental conditions was determined at *p<0.05 and **p<0.01.

TABLE 4

|  | GDNF | | DNSP-11 | |
| --- | --- | --- | --- | --- |
|  | Control | 0.1 ng/ml | Control | 0.1 ng/ml |
| Cell survival | 100 ± 15<br>n = 8 | *158 ± 12<br>n = 8 | 100 ± 16<br>n = 7 | *161 ± 17<br>n = 7 |
| Combined neurite length (um) | 242 ± 12<br>n = 135 | **310 ± 16<br>n = 106 | 222 ± 11<br>n = 139 | **306 ± 23<br>n = 59 |
| Soma size (um$^2$) | 171 ± 4<br>n = 135 | 177 ± 4<br>n = 106 | 168 ± 3<br>n = 139 | 165 ± 5<br>n = 59 |
| Average branches per neuron | 3.8 ± 0.2<br>n = 135 | **4.7 ± 0.2<br>n = 106 | 3.1 ± 0.2<br>n = 139 | **4.4 ± 0.3<br>n = 59 |

Figure 11C:
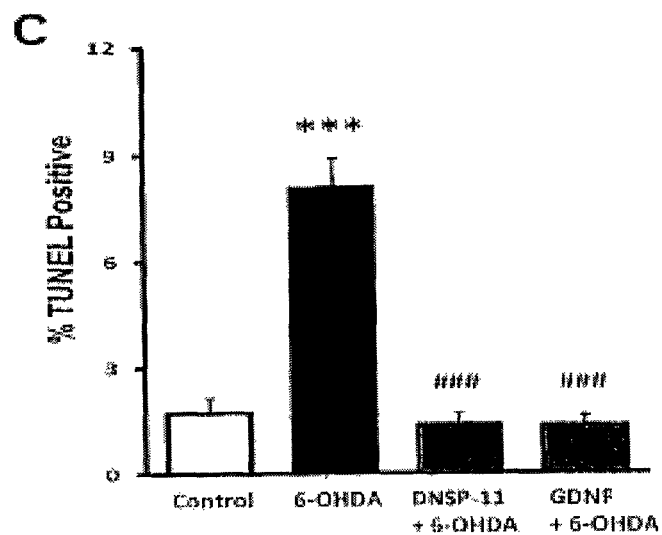
Figure 11D:
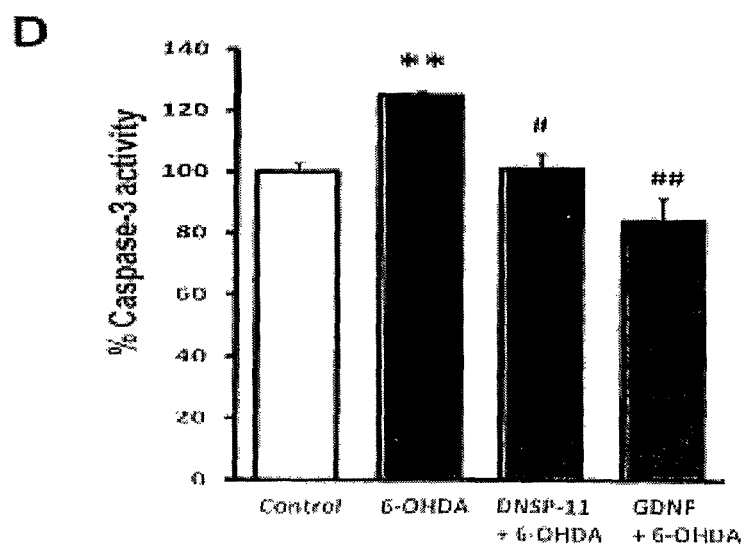

To evaluate DNSP-11's neuroprotective properties, DNSP-11 was compared to GDNF in its protection against 6-OHDA-induced toxicity in the dopaminergic cell line, MN9D. MN9D dopaminergic cells were incubated for 1 hour with either citrate buffer (control), 1 ng/mL of DNSP-11 or GDNF prior to 100 μM 6-OHDA exposure for 15 min. Data are +SD, one-way ANOVA with Tukey's post hoc analysis, *p<0.05, p<0.01, *p<0.001 vs. control; #p<0.05, ##p<0.01, ###p<0.001 vs. 6-OHDA. As seen in FIGS. 11C and D, 100 μM 6-OHDA significantly increased TUNEL staining and caspase-3 activity in MN9D cells (FIGS. 11C and D). Pretreatment with DNSP-11 or GDNF produced a significant reduction in the percent of TUNEL positive cells and caspase-3 activity (FIGS. 11C and D). Thus both DNSP-11 and GDNF protect against 6-OHDA toxicity as demonstrated by reductions in TUNEL staining at 24 h (FIG. 11C) and caspase-3 (FIG. 11D) activity at 3 h after 6-OHDA exposure.

Example 8

Uptake of DNSP-11 into Neurons

Additional studies were carried out to determine if DNSP-11 is actively taken up into dopamine-containing neurons in vivo. A single administration of 30 μg of DNSP-11 was delivered into the rat substantia nigra. Animals were euthanized at 0.5, 1.5, 4, 24 and 48 hrs after injection to visualize distribution of DNSP-11 using antibodies raised against DNSP-11 and the ubiquitinated form of DNSP-11. DNSP-11 antibodies labelled the cytosol and neurites of neurons in the area of the substantia nigra within 30 minutes after injection. DNSP-11 was taken up by neurons in both the substantia nigra, pars reticulata (SNr) and substantia nigra, pars compacta (SNc). The fluorescent immunostaining for DNSP-11, TH and the merger of photomicrographs from each showed that TH-positive dopamine neurons populate the SNc and the ventral tegmental area (VTA). Higher power micrographs from the SNc. DNSP-11 immunostaining revealed uptake into the perikaryon, nucleus, and neurites of TH+ cells.

At 1.5 hrs post-injection, staining for TH+ and DNSP-11 showed overlap in the pars compacta of the substantia nigra and some labeling in the pars reticulata, supporting potential uptake of DNSP-11 into GABAergic neurons. Immunohistochemical staining for DNSP-11 diminished 3 hrs after injection and was absent at 24 hrs and beyond, indicating that there is a rapid uptake of DNSP-11 into neurons.

Example 9

Effect of DNSP-11 on Dopamine Neurochemistry

Prior studies with GDNF have shown robust effects on both potassium and amphetamine-evoked release 28 days after a single injection into the rat substantia nigra (Hebert et al. (1997) *J. Pharm. Exp. Thera.* 282: 760) indicating the functional effects of this trophic factor on dopamine signaling in the normal rat striatum. In the present experiment, 30 μg of DNSP-11 was injected into the right substantia nigra of normal young male Fischer 344 rats. Twenty-eight days after injection, in vivo microdialysis was performed in these animals to investigate dopamine neurochemistry in the ipsilateral striatum. Resting levels of dopamine, 3,4-dihydroxyphenylacetic acid (DOPAC) and homovanillic acid (HVA) were significantly increased by over 100% in the DNSP-11 treated rats as compared to controls (FIG. 12A). These data indicate longer term effects of DNSP-11 on dopamine neuron function, and are analogous to prior results involving GDNF administration in rats and nonhuman primates. Winkler et al. (1996) *J. Neurosci.* 16: 7206; Hebert et al. (1996) *J Pharmacol Exper Ther.* 279: 1181-1190 (1996).

The in vitro studies and in vivo measures of the effects of DNSP-11 led to an investigation of the potential neurorestorative properties of DNSP-11 to damaged dopamine neurons in a unilateral rat model of PD. Fischer 344 rats received dual-site unilateral injections of 6-OHDA to produce extensive destruction of the ascending dopaminergic system that resulted in a greater than 99% depletion of striatal dopamine content ipsilateral to the site of the 6-OHDA injections. Rats were tested 3-4 weeks after the injection of 6-OHDA using low-dose (0.05 mg/kg, i.p.) apomorphine-induced rotational behavior. In rats that rotated greater than 300 turns/60 minutes, 30 μg of DNSP-11 was injected into the ipsilateral substantia nigra. DNSP-11 produced a significant ~50% decrease in apomorphine-induced rotational behavior that was significant 1 week after administration and this effect was maintained for at least 4 weeks after DNSP-11 (FIG. 12B). At 5 weeks, the substantia nigra and striatum from each rat was analyzed by high performance liquid chromatography coupled with electrochemical detection. A single injection of DNSP-11 was found to significantly increase levels of dopamine and the dopamine metabolite, DOPAC, by ~100% in the substantia nigra, indicating that DNSP-11 has a powerful neurotrophic-like restorative effect on dopamine neurons in this animal model of late stage PD (FIG. 12C).

As shown in FIG. 12A, 28 days after DNSP-11 or citrate buffer vehicle was delivered to the nigral cell bodies, the DNSP-11 treatment group showed significantly higher basal neurochemical concentrations of DA, DOPAC and HVA.

Basal DA increased from 26.0±2.7 nM in the vehicle treatment group to 45.8±7.7 nM in the DNSP-11 treatment group ($t_{(31)}$=2.255, p=0.0314). Basal concentrations of DOPAC increased from 3355±338 nM in the vehicle group to 6544±836 nM in the DNSP-11 group ($t_{(31)}$=3.293, p=0.0025), and HVA, increased from 2419±251 nM with vehicle treatment to 4516±502 nM with DNSP-11 treatment ($t_{(30)}$=3.588, p=0.0012). All data were analyzed using a two-tailed unpaired t-test * p<0.05. FIG. 12B shows the results of assessment of apomorphine (0.05 mg/kg) induced rotational behavior prior to infusion treatment (Pre) and once weekly for 4 weeks after DNSP-11 or vehicle treatment. Drug-induced rotational behavior is expressed as a percentage of vehicle treatment and showed a significant decrease in rotational behavior beginning one week after DNSP-11 treatment that lasted for all 4 weeks post DNSP-11. The data were analyzed using a one-way ANOVA for repeated measures ($F_{(4,39)}$=4.807, p=0.0005) with Bonferroni's multiple comparison test * p<0.05,  p<0.01, * p<0.001. FIG. 12C shows that DNSP-11 treatment significantly increased levels of DA, (74%) and DOPAC (132%) in the substantia nigra of unilateral 6-OHDA-lesioned rats. DA content was determined to be 34.7±6.4 ng/g in the vehicle treatment group and 59.1±7.3 ng/g in the DNSP-11 treatment group ($t_{(13)}$=2.521, p=0.0265). DOPAC tissue content was determined to be 7.10±1.40 ng/g in the vehicle treatment group and 16.48±4.01 ng/g ($t_{(13)}$=2.33, p=0.0364) in the DNSP-11 treatment group. All data were analyzed using a two-tailed unpaired t-test, * p<0.05.

Example 10

Interaction of DNSP-11 with Protein Partners

In order to identify the interactions of DNSP-11 with protein partners and to gain insight into the cellular mechanisms involved with the actions of DNSP-11, a pull-down assay was performed with homogenate from isolated substantia nigra of normal young Fischer 344 rats. Cytosolic and membrane fractions were collected and incubated with biotinylated DNSP-11 for 30 minutes. Bound proteins were pulled down by strepavidin magnetic beads, extensively washed to remove non-specific binders, eluted with solubilization/rehydration buffer and separated by 2D-PAGE.

Specifically, a solution of 25 μL GFRα1 (1 mg/mL) was incubated with 50 μL of Dynabeads® (Invitrogen) in wash and bind buffer (0.1M sodium phosphate, pH 8.2, 0.01% Tween® 20) for 10 minutes at room temperature. The beads were then washed three times in 100 μL of wash and bind buffer. 2 μg of GDNF was added and incubated for 1 hour at 4° C. 25 μL GFRα1 (1 mg/mL) was incubated with 40 μg of biotinylated DNSP-11 (bDNSP-11) for 1 hour at 4° C. They were then added to 50 μL of hydrophilic streptavidin magnetic beads (New England Biolabs) and incubated for an hour at 4° C.

Several spots were observed in both the cytosolic and membrane fractions, indicating that DNSP-11 is able to bind proteins found within the substantia nigra. To identify these binding partners, protein bands were excised from the gels, trypsin digested, and analyzed by MALDI-TOF mass spectrometry. From these preliminary studies, approximately 20 proteins were identified. Of these, glyceraldehyde-3-phosphate dehydrogenase (GAPDH), a protein with a link to PD and apoptosis, was identified. This result was confirmed by in vitro pull down assays with pure GAPDH and DNSP-11.

Figure 13:
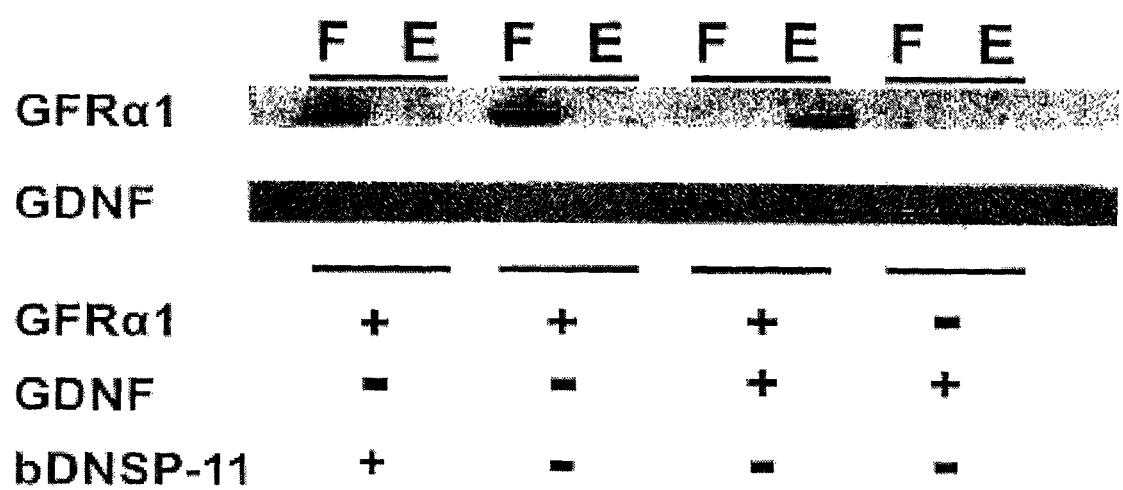
FIG. 13 depicts the interactions of DNSP-11 with protein partners.

In addition, a pull-down assay of DNSP-11 with GFRα1 indicated that the two molecules do not interact, like mature GDNF (FIG. 13; F-Flow through, E-Elution). Moreover, the absence of interaction between GFRα1 with DNSP-11 is supported by ELISA.

Figure 14:
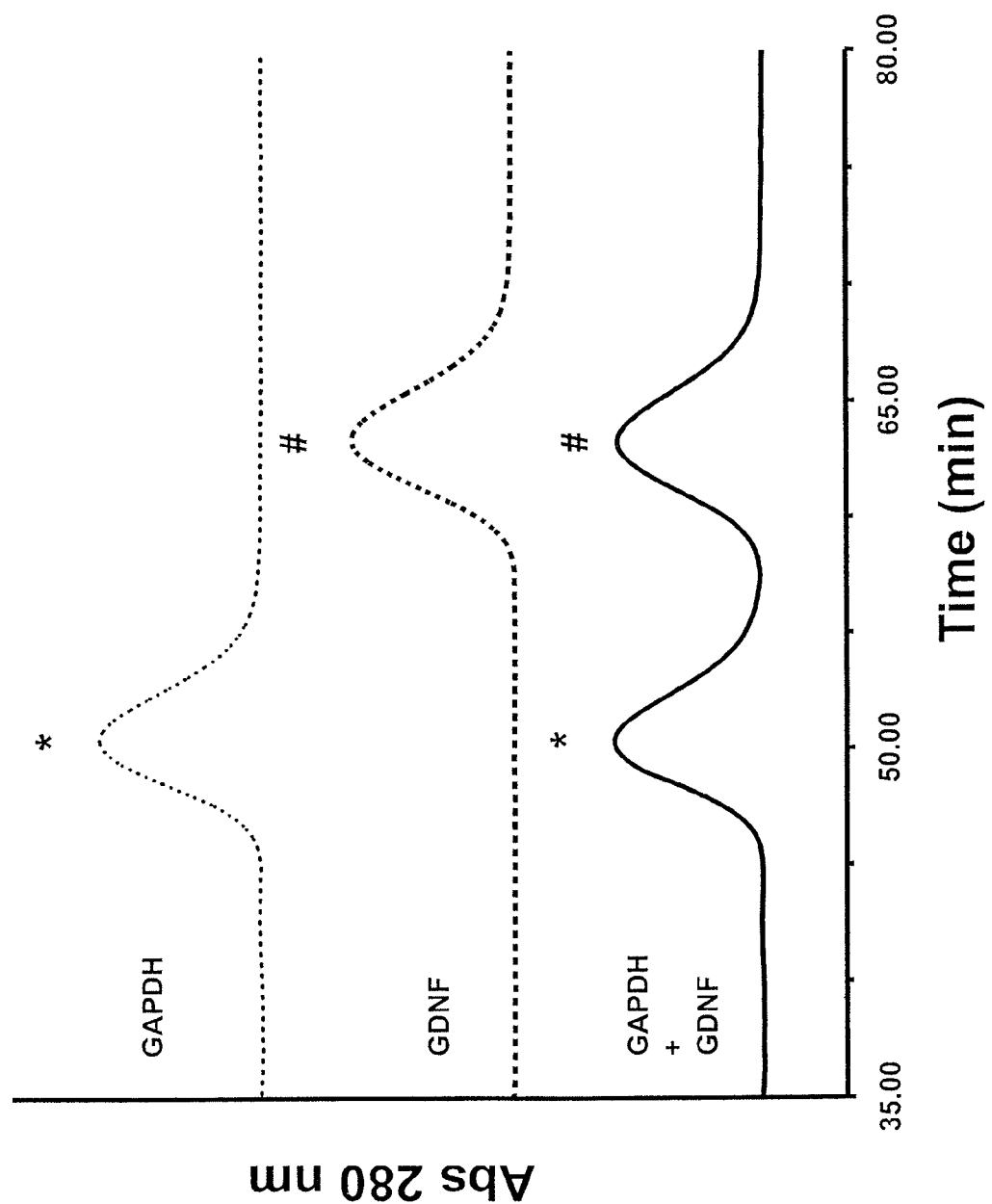
FIG. 14 depicts the gel filtration analysis of the interaction between GAPDH and GDNF.

A gel filtration study was performed using a 120 mL Sephacryl S-200 column at a constant 1 mL/min flow rate. Individual 300 μM solutions of GAPDH (~150 kDa; FIG. 14, dotted line) or GDNF (~30 kDa; FIG. 14, dashed line) eluted at expected retention times for their sizes of 50 min (FIG. 14, star) and 64 min (FIG. 14, pound sign), respectively. When a pre-equilibrated (1 h), equimolar solution of GAPDH and GDNF was analyzed by gel filtration chromatography, two equally intense peaks were observed (FIG. 14, solid line) with retention times identical to the individual solutions. These data demonstrate that GDNF does not interact with GAPDH in solution, thereby providing evidence that DNSP-11 has an independent mechanism of action relative to mature GDNF.

Taken together, these data indicate that DNSP-11 exhibits potent neurotrophic actions analogous to GDNF, but likely signals through pathways that do not directly involve the GFRα1 receptor.

The foregoing examples demonstrate that DNSP-11 shares many physiological and neurotrophic properties with mature GDNF, including neuroprotection and promoting differentiation in primary dopamine neuron cell cultures; increasing dopamine release and metabolism in vivo; and decreasing apomorphine-induced rotations and enhancing dopamine function in the substantia nigra of 6-OHDA lesioned rats.

Example 11

DNSP-11 Solubility and Stability

The backbone secondary structure of DNSP-11 was examined using circular dichroism spectroscopy in the far-UV region (CD; University of Kentucky Center of Structural Biology). The DNSP-11 spectrum (FIG. 15A) displayed a broad minimum mean residue ellipticity (MRE) at 200 nm, indicative of a peptide that it is dynamic and samples multiple confirmations. Small shoulders between 208-230 nm indicate that DNSP-11 appears to be sampling polyproline II and other helical structures. Collectively, the spectrum of DNSP-11 shows that it has characteristics of typical small, soluble, functional peptides of similar length.

Figure 15B:
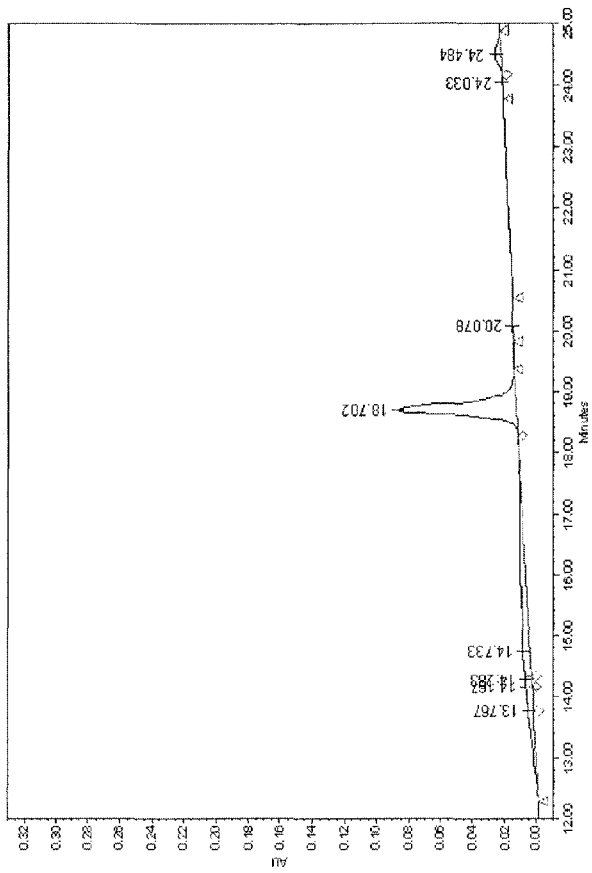
FIGS. 15A-C depict the solubility and stability of DNSP-11 at various storage and experimental conditions.
Figure 15C:
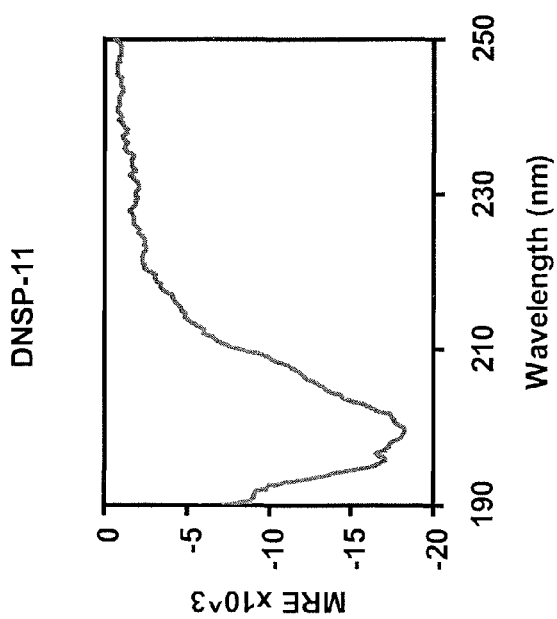
Figure 15A:
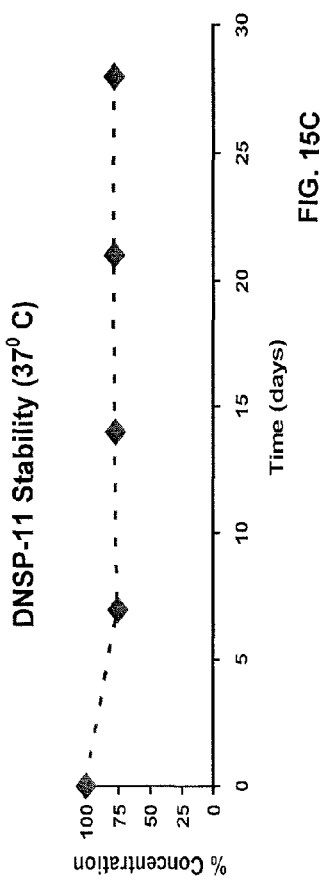

Reverse Phase HPLC(RP-HPLC; FIG. 15B); University of Kentucky Center of Structural Biology) and electrospray mass spectrometry (University of Kentucky Mass Spectrometry Facility) were used to monitor at the stability of DNSP-11. DNSP-11 was stored in citrate buffer (10 mM Citrate+150 mM NaCl, pH 5.0) at −80° C. and 37° C. for 30 days. These temperatures were chosen based on their relevance to long term storage and use in future studies. The results of these studies showed that the peptides were stable at both temperatures for one month without any appreciable loss of peptide (FIG. 15C).

Figure 16:
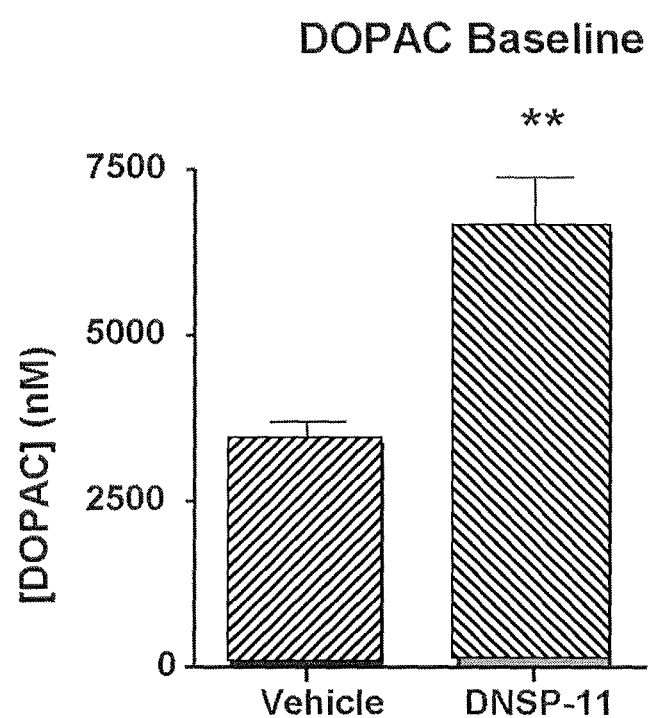
FIG. 16 shows the effects of citrate vehicle or DNSP-11 on resting levels of DOPAC one month after a single infusion.

Our analysis of the effects of DNSP-11 on dopamine neurons in the nigrostriatal system of the brain of young adult F344 rats at 28 days following a single injection of the peptide, demonstrated a surprising effect, i.e., an increase in basal tissue levels of the dopamine metabolite 3,4-dihydroxyphenylacetic acid (DOPAC, see FIG. 16). The 100% increase in DOPAC was unprecedented in our numerous experiments over the past 20 years. In fact, we have never seen a dopamine-altering agent, which increases the metabolism of dopamine by 100% and this effect was seen to persist for one month after a single injection of DNSP-11 into the substantia nigra, which is the source of the dopamine-containing fibers measured in the striatum. GDNF, which augmented the evoked release of dopamine by over 100%, increased basal levels of DOPAC by only 20-25% in young and aged rats (Herbert et al. *J. Pharmacol. Exp. Therapeut.* (1996) 279:1181-1190, and Hebert and Gerhardt, *J. Pharmacol. Exp. Therapeut.* (1997) 282:760-768). Based on the results presented herein, and the knowledge that DOPAC is produced when dopamine is metabolized by monoamine oxidase B, (an enzyme on the outer membrane of mitochondria (Edmondson et al, *Curr. Med. Chem* (2004) 11(15:1983-93) and then the product of this reaction is metabolized by aldehyde dehydrogenase (which resides in the cytosol of cells) we reasoned that DNSP-11 increases mitochondrial functions and thereby increases monoamine oxidase levels. The following examples address this.

Example 12

DNSP-11: Distribution, Uptake and Half-Life in the Brain

To assess the distribution, uptake and degradation of DNSP-11 in the brain, young adult male F344 rats, as a test organism, received injections of 30 µg DNSP-11 in the substantia nigra, hippocampus or cortex. They were euthanized by anesthesia overdose at various time points from 30 minutes to 48 hrs later and perfused through the heart with saline followed by paraformaldehyde.

Our standard published procedures for immunocytochemical staining were used (e.g. Gash D M et al., *J Comp Neurol.* 1995 Dec. 18; 363(3):345-58, Grondin et al., 2002; Ai et al., 2003). A polyclonal antibody was generated against DNSP-11 in rabbits (Alpha Diagnostic International, San Antonio, Tex.). Endogenous peroxidases were inactivated by incubation with 0.2% hydrogen peroxide ($H_2O_2$) for 10 minutes and background blocked with 4% normal serum, 1% bovine serum albumin (BSA) for 1 hour. Free floating sections were incubated in primary antisera. Sections were then exposed to the appropriate biotinylated IgG (Vecto Labs, Burlingame, Calif.) for 1 hour and then incubated in avidin-biotin-peroxidase complex using Elite ABC Vectastain Kits (Vector Labs) for 1 hour. Some sections were double-labeled using procedures following our published procedures for immunocytochemical staining to identify cells with two markers (e.g. Ai et al., 2003).

Controls for immunostaining included the omission of primary antibodies and replacement of primary antibodies with normal serum of the same species.

Results: A 30 µg bolus of DNSP-11 injected into the mid-substantia nigra region using stereotaxic procedures spreads ~3 mm in the anterior-posterior plane and up to ~2 mm in the medial-lateral plane (FIG. 17) to cover most of the pars compacta component of the nigra. DNSP-11 is taken up in the first 30 minutes following injection by neurons and their axonal and dendritic processes. It is found in the cytoplasm and then perinuclear area and nucleus. At 24 hours after injection, some residual DNSP-11 can still be detected. There was no evidence of DNSP-11 by 48 hours post peptide administration.

Stereotaxic injections of 30 µg DNSP-11 were also made into the striatum, hippocampus and cortex. Uptake was observed into neurons in both areas. Pyramidal neurons in the cortex accumulated DNSP-11.

In summary, DNSP-11 is taken up within 30 minutes by neurons in all brain areas evaluated. The uptake sites appear to be specific for axons, dendrites, synaptic terminals and perikarya of nerve cells. DNSP-11 immunostaining is found in the cytoplasm and then in the nucleus. The half-life of DNSP-11 in the rat brain is under 24 hours. The areas of the brain studied (substantia nigra, striatum, hippocampus and cortex) have major roles in cognitive and motor functions. Tropic actions of DNSP-11 could protect these brain areas from injury and/or promote restoration from disease and injury processes.

Example 13

DNSP-11 Induced Changes in Genes Regulating Mitochondria/Functions

Changes in expression of mitochondrial-associated genes in the substantia nigra (SN) of three young adult (5 month old) male F344 rats 48 hours following bilateral intranigral injections of DNSP-11 into the substantial nigra was assessed as follows.

A 3 µg/µl DNSP-11 peptide solution was prepared in citrate buffer and filter sterilized. Stereotaxic injections were made of 30 µg DNSP-11 in 10 ul citrate buffer into the substantia nigra on each side of the brain. Controls received 10 µg injections of vehicle. Forty-eight hours later, the animals were euthanized, the brains quickly recovered and sectioned so that the bilateral SN could be dissected out as one block of tissue and snap frozen in liquid nitrogen. RNA was extracted from the SN samples for gene array analysis, which was conducted on Affymetrix Version II chips. A gene chip was run for each of the six rats: three bilateral vehicle recipients, three bilateral 30 µg DNSP-11 recipients.

Genes regulating mitochondrial functions were identified as the subset of genes on the microarray in the peptide-treated group having expression levels that were significantly increased or decreased as compared to the controls (Table 5). Fourteen genes were significantly up-regulated and five were significantly down-regulated in DNSP-11 recipients. One gene with increased expression was Monoamine Oxidase B, a finding consistent with the higher DOPAC levels mentioned earlier. A number of other genes with increased expression are associated with protection against oxidative damage: glutathione/glutaredoxin, glutathione peroxidase and thioredoxin (Koehler et al., *Antioxid Redox. Signal.*, 8(5-6):813-22 (2006); Comhair & Erzurum *Antioxid Redox Signal.*, 7(1-2):72-9. (2005)). Catalase is an important enzyme converting the strong oxidant hydrogen peroxide to water- and oxygen (Calderon I L et al., Catalases are NAD(P)H-dependent teliurite reductases. *PLoS ONE.* 1:e70 (2006 Dec. 20)). Peroxyredoxin is another antioxidant (Rhee, Chae & Kim, *Free Radic Biol Med.* 2005 Jun. 15; 38(12):1543-52. Epub (2005 Mar. 24)). Increased levels of Park 7 (DJ-1) are protective against Parkinson's disease (Thomas & Beal, *Hum Mol. Genet.* 16 Spec No. 2:R183-94 (2007 Oct. 15)) and increase levels of Presenilin 1 are believed to be protective against Alzheimer's disease (Das, *Front Biosci.* 13:822-32 9 (2008 Jan. 1)). In both instances, it is a decreased or mutant form of the gene that is closely linked to neurodegenerative diseases. The cytochrome c oxidase subunits are components of the terminal respiratory complex producing energy via oxidative phosphorylation.

TABLE 5

Changes in expression level post DNSP-11 delivery

| SYMBOL | DESCRIPTION | PEPTIDE | CONTROL | P-VALUE | FOLD CHANGE |
|---|---|---|---|---|---|
| GLRX2 | glutaredoxin 2 | 3618.7 | 3472.2 | <0.001 | 1.09 |
| CASP8 | caspase 8, apoptosis-related cysteine peptidase | 219.4 | 178.1 | 0.006 | 1.25 |
| TXN2 | thioredoxin 2 | 1511.9 | 1378.5 | 0.010 | 1.10 |
| MAOB | monoamine oxidase B | 2199.8 | 1974.2 | 0.012 | 1.13 |
| COX6A2 | cytochrome c oxidase subunit VIa polypeptide2 | 814.1 | 520.6 | 0.014 | 1.75 |
| GPX7 | glutathione peroxidase 7 | 194.2 | 183.8 | 0.015 | 1.19 |
| CAT | catalase | 2828.2 | 271a.0 | 0.015 | 1.09 |
| PRDX5 | peroxiredoxin 5 | 5569.8 | 4790.1 | 0.020 | 1.13 |
| PSEN1 | presenilin 1 (Alzheimer disease 3) | 673.5 | 563.2 | 0.022 | 1.16 |
| CASP3 | caspase 3, apoptosis-related cysteine peptidase | 421.4 | 367.5 | 0.024 | 1.18 |
| COX17 | COX17 cytochrome c oxidase assembly homolog (S. cerevisiae) | 2326.1 | 2017.8 | 0.025 | 1.11 |
| PARK7 | DJ-1 protective against Parkinson's disease | 5299.2 | 5159.4 | 0.032 | 1.02 |
| COX6B1 | cytochrome c oxidase subunit VIb polypeptide 1 (ubiquitous) | 7869.7 | 7536.6 | 0.044 | 1.04 |
| NDUFA7 | NADH dehydrogenase (ubiquinone) 1 alpha subcomplex, 7, 14.5 kDa | 3125.4 | 2943.0 | 0.046 | 1.07 |
| APP | amyloid beta (A4) precursor protein (peptidase nexin-II, Alzheimer disease) | 9734.4 | 10117.2 | 0.006 | −1.08 |
| MAPK9 | mitogen-activated protein kinase 9 | 770.7 | 930.0 | 0.007 | −1.21 |
| MAPK10 | mitogen-activated protein kinase 10 | 505.0 | 552.8 | 0.008 | −1.08 |
| BACEI | beta-site APP-cleaving enzyme 1 | 451.6 | 510.6 | 0.016 | −1.09 |
| MAP2K4 | mitogen-activated protein kinase kinase 4 | 2422.4 | 2744.4 | 0.043 | −1.12 |

The caspases having increased expression are associated with apotosis (Kataoka, Crit. Rev Immunol. 25(1):31-58 (2005); Vassar, Neuron 54(5):671-3 (2007)). Without wishing to be bound by theory, the increased expression of low levels capases may reflect a nonspecific inflammatory reaction to the mild physical injury induced by the needle track and injection of material into the substantia nigra.

The foregoing results indicate that DNSP-11 treatment significantly effects the expression of genes regulating mitochondrial functions. The changes in gene expression would be neuroprotective against free radical oxidative damage to mitochondria. This would decrease mitochondrial wear and tear from oxidative respiratory processes producing energy, increasing the functional lifespan of mitochondria in a neurons and synapses.

Example 14

DNSP-11 Increases State III Mitochondria/Respiration in the Rat Nigrostriatal System As our previous studies had demonstrated that injections of 30 μg DNSP-11 into the substantia nigra had marked effects 28 days post administration with elevated levels of dopamine and dopamine metabolites in the nigrostriatal system (substantia nigra and its projections to the striatum), we quantified the effects of DNSP-11 on mitochondria respiration and enzyme activity in the nigrostriatal system of young adult F344 rats at 28 days post injection.

Six five-month-old male F344 rats received bilateral intranigral injections of 30 μg DNSP-11. Six age and sex-matched controls received injections of the same volume of vehicle (citrate buffer). Twenty-eight days after test material administration, the animals were euthanized by $CO_2$ anesthesia and the brain samples rapidly dissected. The striatum and substantia nigra were isolated quickly and carefully using a rat brain matrix for F344 rats.

Mitochondrial respiration was assessed using a miniature Clark-type electrode, in a sealed, thermostatic and continuously stirred chamber. Mitochondria were added to the chamber to yield a final protein concentration of 1 mg/ml. The substrate concentrations were 5.0 mM/2.5 mM for glutamate/malate and pyruvate/malate or 10 mM for succinate +2.5 μM rotenone or α-glycerophosphate. State 3 respiration was initiated by the addition of 150 ηmols ADP. The respiratory control ratio was calculated as respiration in the presence of ADP (state 3)/respiration in absence of ADP (state 4). ADP/0 ratios were determined by dividing the amount of ADP phosphorylated during State III respiration by the amount of oxygen consumed. NAD-linked substrates, e.g. glutamate and pyruvate, utilize complexes I, III, IV in their oxidation, succinate utilizes complexes II, III, IV and α-glycerophosphate utilizes III, IV. Thus impaired oxidation of NAD-linked substrates, but normal oxidation of succinate or α-glycerophosphate implies a defect at the level of complex I. Impaired oxidation of both NAD-linked and succinate oxidation implies a defect in both complex I and II and/or in complex III and IV which can be elucidated by the use of α-glycerophosphate.

The chamber was also equipped with fluorescence/absorbance probes which allow us to also measure simultaneously ROS production in real-time with all other parameters. ROS production was measured using the $H_2O_2$ indicator dichlorodihydrofluorescein diacetate ($H_2$DCFDA, Molecular Probes). Ten μM $H_2$DCFDA, which is made fresh before each use, was added to the chamber and the relative amount of mitochondria) $H_2O_2$ and free radical production measured as an increase in fluorescence. Again the same rationale as above can be used to pinpoint the source of ROS production. Additionally, ROS production was monitored over time in a Synergy HT plate reader or a Shimadzu RF-5301 spectrofluorimeter with stirred and water-jacketted cuvett holders (excitation 490 μm, emissions 526 ηm; ex550ηm, em590ηm, respectively) at 37° C. for 15 min in the presence of 10 μM $H_2$DCFDA or Amplex Red, a $H_2O_2$ indicator that is extramitochondrial. Controls include the addition of the electron transport chain inhibitor antimycin (complex III inhibitor, yields maximum ROS production independent of ΔΨ), oligomycin (inhibits ATPase yielding maximum ΔΨ-dependent ROS production) and the uncoupler FCCP (inhibits all ΔΨ-dependent ROS production).

The mitochondria are freeze-thawed and sonicated three times for measuring all the complexes activities. Complex I (NADH dehydrogenase) assay is performed in 2.5 mM $KPO_4$ buffer (pH 7.2) containing mitochondrial protein (6 μg), 5 mM $MgCl_2$, 1 mM KCN, 1 mg/ml BSA, and 150 μM NADH at 30° C., the reaction initiated by addition of coenzyme Q-1 (50 μM). In this reaction ubiquinone 1 was the final electron acceptor. The decrease in NADH absorbance at 340 ηm was monitored. The assay was also performed in the presence of rotenone (10 μM) to determine the rotenone-insensitive and the rotenone-sensitive complex I enzyme activity. Complex II (succinate dehydrogenase) activity was measured by the rate of reduction of 2,6-Dichloroindophenol. The reaction mixture contained 100 mM $KPO_4$ buffer, 20 mM succinate, 10 μM EDTA, 0.01% Triton, 1 μg/100 μl coenzyme Q2 containing mitochondria) protein (6 μg) at 30° C. and the reaction was initiated by the addition of 0.07% 2,6-Dichloroindophenol. Decreased in absorbance was monitored at 600 ηm. Complex IV (cytochrome c oxidase) activity was measured in 10 mM $KPO_4$ buffer and 50 μM reduced cytochrome c. The reaction was initiated by addition of 6 μg mitochondria) protein. Rate of oxidation of cytochrome c was measured by measuring the decrease in absorbance of reduced cytochrome c, observed at 550 nm.

Figure 18B:
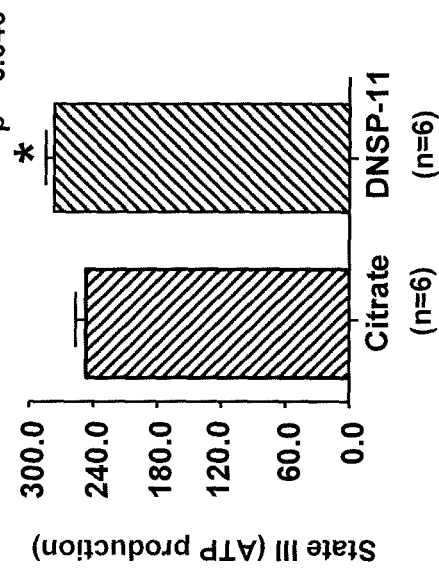
FIG. 18 shows the DNSP-11 increased State III oxygen consumption vs. vehicle in both the SN and striatum, 28 days post bilateral intrnigral injections (*$p<0.05$ vs control, two-tailed, unpaired tests). (A) Substantia nigra 28 days; (B) Striatum 28 days.
Figure 18A:
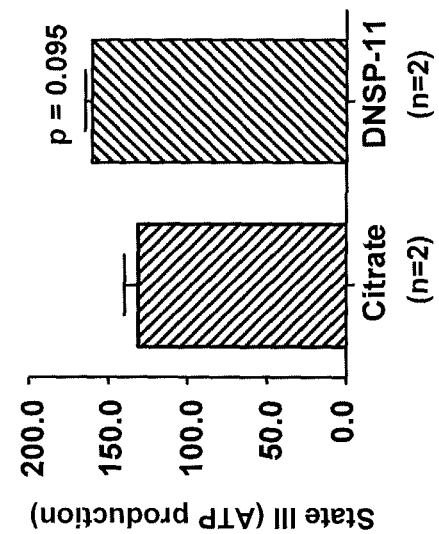

As shown in FIG. 18, there was a trend towards an increase in State III oxidative phosphorylation at 28 days post treatment in the substantia nigra. However, with an n=2, the difference was not significant with a two-tailed t-test. The effects reached statistical significance in the striatum, which is heavily innervated by dopamine fibers from the substantia nigra forming synapses on striatal medium spiny neurons. Evidence described in Example 12 indicates that DNSP-11 was taken up within 30 minutes into neuritic processes and cell bodies of neurons. Soon thereafter, immunoreactive DNSP-11 was found in the nucleus. The effects at 28 days on dopamine and metabolite levels and on mitochondria demonstrate that DNSP-11 treatment initiates genetic changes that last for long periods, at least one month, and without wishing to be bound by theory, this may occur perhaps through receptors involving transcribing factors.

Figure 17:
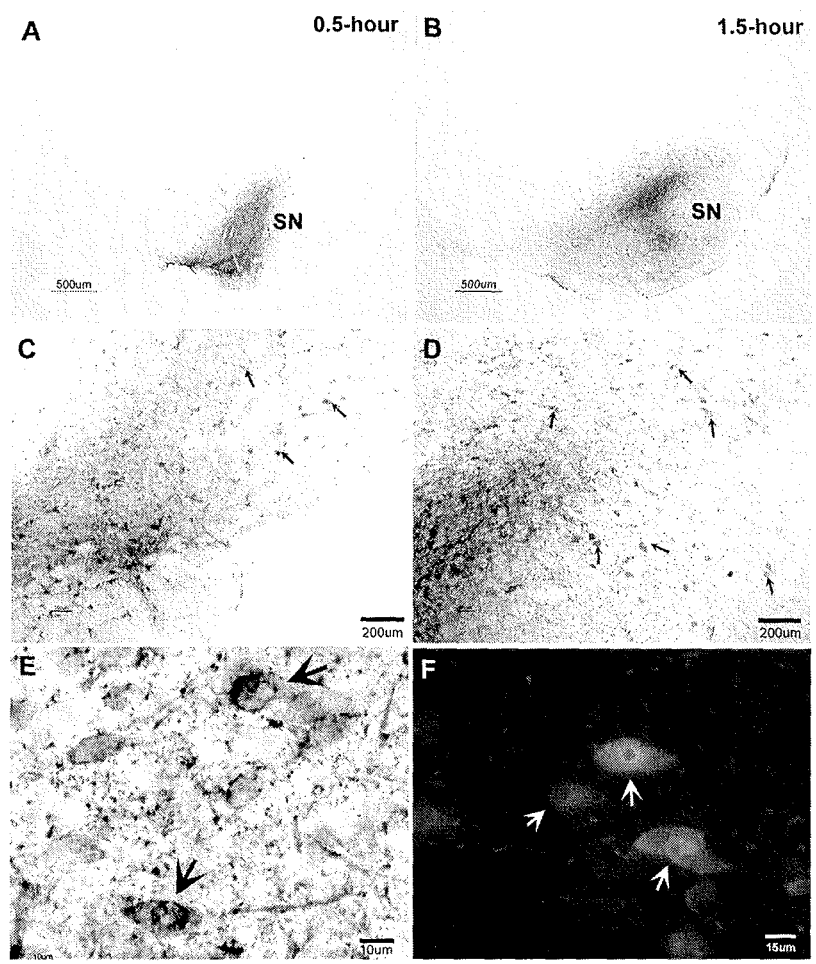
FIG. 17 shows the broad distribution of DNSP-11 in the rat substantia nigra region of the midbran within 30 minutes of DNSP-11 injection (panels A-F).

Within 30 minutes following a 30 ug injection of DNSP-11 into the F344 rat substantia nigra, the broad distribution of the compound through the substantia nigra (SN) region of the midbrain was evident (FIG. 17, panels A, B). At higher magnification (FIG. 17 panels C, D) uptake of the peptide by neurons (arrows) could be discerned. At very high magnification (FIG. 17 panel E), punctuate-immunoreactive staining of DNSP-11 was present in neuritic processes, cytoplasm and the perinuclear area of the cell body (arrows). The pattern of immunoreactivity was similar at 90 minutes post injection (FIG. 17 panel B), with prominent labeling in DNSP-11 in cells and neuritic processes (FIG. 17, panel D). Immunostaining was more sensitive using fluorescent techniques (FIG. 17, panel F), highlighting DNSP-11 immunoreactivity in the cytoplasm and nuclei of neurons. The cells in F were double-labeled for the neuronal marker NeuN and DNSP-11.

By improving mitochondrial functions in neurons and their synapses, DNSP-11 treatment could significantly restore neural networks affected in neurodegenerative diseases, including Alzheimer's disease and Parkinson's disease, improving cognitive functions in the former and improved motor functions in the latter.

Example 15

The in vitro studies and in vivo measures of the neurotrophic/mitochondrogenic effects of DNSP-11 led us to investigate the potential neurorestorative properties of DNSP-11 to damaged dopamine neurons in a unilateral rat model of PD.

Figure 19:
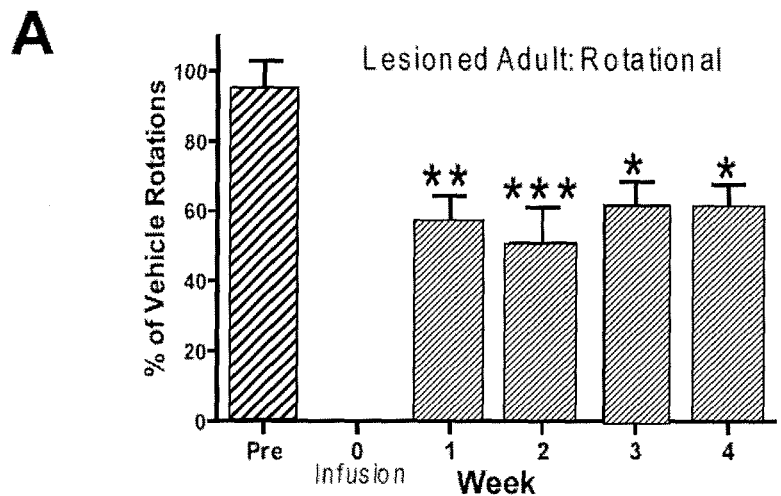
FIG. 19 demonstrates that DNSP-11 produced a significant, about 50%, decrease in apomorphine-induced rotational behavior (A) and significantly increased levels of dopamine and the dopamine metabolite, DOPAC, by about 100% in the substantia nigra (B).
Figure 19:
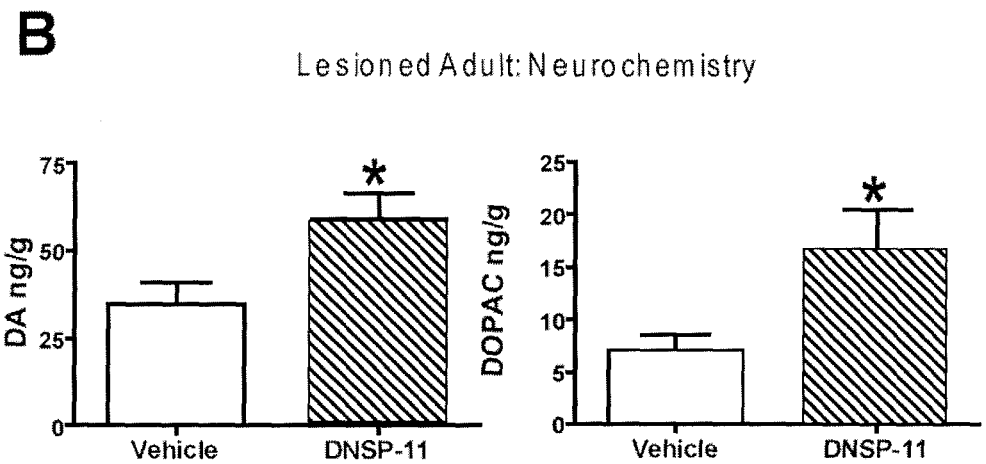

Fischer 344 rats received dual-site unilateral injections of 6-OHDA to produce extensive destruction of the ascending dopaminergic system that resulted in a greater than 99% depletion of striatal dopamine content ipsilateral to the site of the 6-OHDA injections. Rats were tested 3-4 weeks after the injection of 6-OHDA using low-dose (0.05 mg/kg, i.p.) apomorphine to induce rotational behavior. In rats that rotated greater than 300 turns/60 minutes, 30 μg of DNSP-11 was injected into the ipsilateral substantia nigra. DNSP-11 produced a significant ~50% decrease in apomorphine-induced rotational behavior that was significant 1 week after administration and this effect was maintained for at least 4 weeks after DNSP-11 (FIG. 19A). At 5 weeks, the substantia nigra and striatum from each rat was analyzed by high performance liquid chromatography coupled with electrochemical detection. A single injection of DNSP-11 was found to significantly increase levels of dopamine and the dopamine metabolite, DOPAC, by ~100% in the substantia nigra, supporting that DNSP-11 has a powerful neurotrophic-like/mitochondrogenic restorative effect on dopamine neurons in this animal model of late stage PD (FIG. 19B).

In summary, the evidence reported in this patent application demonstrates the ability of DNSP-11 treatment to improve mitochondrial functions and supports the ability of DNSP-11 treatment to promote behavioral restoration in Alzheimer's disease, Parkinson's disease and aging processes.

Our results demonstrate that DNSP-11 is taken up by neurons in the cortex, hippocampus and substantia nigra, areas important in cognitive and motor functions;

Our results demonstrate that DNSP-11 significantly increases the expression of genes associated with mitochondrial functions in the brain, including genes for proteins that protect mitochondria from oxidative damage leading to functional deterioration;

Our results demonstrate that DNSP-11 increases energy production in brain mitochondria for extended periods.

Increased energy production in mitochondria in synapses is posited to promote restoration of neural circuitry leading to restoration of cognitive and motor functions.

While the present invention has been described with reference to specific embodiments, this application is intended to cover those various changes and substitutions that may be made by those of ordinary skill in the art without departing from the spirit and scope of the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications cited herein are hereby incorporated by reference in their entirety.

What is claimed is:

1. A method for promoting the survival and/or function of dopaminergic neurons, comprising administering to a subject in need thereof a pharmaceutically effective amount of a composition comprising at least one of the following peptides:
   (a) a purified Amidated Dopamine Neuron Stimulating peptide (ADNS peptide) comprising the amino acid sequence ERNRQAAAANPENSRGK-amide (SEQ ID NO: 2);
   (b) a purified ADNS peptide comprising the amino acid sequence FPLPA-amide (SEQ ID NO: 3); and
   (c) a purified ADNS peptide comprising the amino acid sequence PPEAPAEDRSL-amide (SEQ ID NO: 4)
   wherein the composition is administered to a subject having at least one condition selected from the group consisting of Parkinson's Disease, Alzheimer's disease, and Amyotrophic Lateral Sclerosis (ALS); and
   wherein the composition is administered in an amount sufficient to increase the level of at least one of dopamine and a dopamine metabolite in the subject.

2. The method of claim 1 wherein the composition comprises a purified ADNS peptide comprising the amino acid sequence PPEAPAEDRSL-amide (SEQ ID NO: 4).

3. A method for treating a brain disease or injury resulting in dopaminergic deficiencies, comprising administering to a subject in need thereof a pharmaceutically effective amount of a composition comprising at least one of the following peptides:
   (a) a purified Amidated Dopamine Neuron Stimulating peptide (ADNS peptide) comprising the amino acid sequence ERNRQAAAANPENSRGK-amide (SEQ ID NO: 2);
   (b) a purified ADNS peptide comprising the amino acid sequence FPLPA-amide (SEQ ID NO: 3); and
   (c) a purified ADNS peptide comprising the amino acid sequence PPEAPAEDRSL-amide (SEQ ID NO: 4);
   wherein said composition further comprises at least one of a pharmaceutically acceptable vehicle, excipient, and diluent,
   wherein the brain disease or injury is at least one condition selected from the group consisting of Parkinson's Disease, Alzheimer's disease, and Amyotrophic Lateral Sclerosis (ALS); and
   wherein the composition is administered in an amount sufficient to increase the level of at least one of dopamine and a dopamine metabolite in the subject.

4. The method of claim 3 wherein the composition comprises a purified ADNS peptide comprising the amino acid sequence PPEAPAEDRSL-amide (SEQ ID NO: 4).

5. A method of increasing levels of at least one of dopamine and a dopamine metabolite in a subject having damaged dopamine neurons comprising
   administering a pharmaceutically effective amount of a composition comprising a purified peptide comprising the amino acid sequence PPEAPAEDRSL-amide (SEQ ID NO: 4) and at least one of a pharmaceutically acceptable vehicle, excipient, and diluent,
   wherein the damaged dopamine neurons are associated with at least one condition selected from the group consisting of Parkinson's Disease, Alzheimer's disease, and Amyotrophic Lateral Sclerosis (ALS); and
   wherein the composition is administered in an amount sufficient to increase the level of at least one of dopamine and a dopamine metabolite in the subject.

6. The method of claim 1, wherein the level of at least one of dopamine and a dopamine metabolite is measured by microdialysis.

7. The method of claim 3, wherein the level of at least one of dopamine and a dopamine metabolite is measured by microdialysis.

8. The method of claim 5, wherein the level of at least one of dopamine and a dopamine metabolite is measured by microdialysis.

* * * * *